US006596545B1

(12) United States Patent
Wagner et al.

(10) Patent No.: US 6,596,545 B1
(45) Date of Patent: *Jul. 22, 2003

(54) MICRODEVICES FOR SCREENING BIOMOLECULES

(75) Inventors: Peter Wagner, Belmont, CA (US); Dana Ault-Riche, Palo Alto, CA (US); Steffen Nock, Redwood City, CA (US); Christian Itin, Menlo Park, CA (US)

(73) Assignee: Zyomyx, Inc., Hayward, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/353,554

(22) Filed: Jul. 14, 1999

Related U.S. Application Data

(63) Continuation-in-part of application No. 09/115,397, filed on Jul. 14, 1998.

(51) Int. Cl.[7] ............................................. G01N 33/543
(52) U.S. Cl. ..................... 436/518; 435/4; 435/7.1; 435/287.1; 435/288.2; 435/288.5; 435/6; 436/514; 422/55; 422/58; 427/261; 427/287; 427/387; 427/407.2
(58) Field of Search ............... 548/303.7, 303, 548/303.1; 427/261, 287, 387, 407.2; 435/4, 7.1, 131, 288.2, 288.5, 287.1, 6; 436/514, 518; 422/55, 58

(56) References Cited

U.S. PATENT DOCUMENTS

| 4,071,409 A | 1/1978 | Messing et al. | |
| 4,562,157 A | 12/1985 | Lowe et al. | 435/291 |
| 4,690,715 A | 9/1987 | Allara et al. | 148/6.15 |
| 4,722,896 A | 2/1988 | Kadish et al. | |
| 4,908,112 A | 3/1990 | Pace | 204/299 |
| 4,973,493 A | 11/1990 | Guire | 427/2 |
| 4,987,032 A | 1/1991 | Miyasaka et al. | |

(List continued on next page.)

FOREIGN PATENT DOCUMENTS

| WO | WO 93/21528 | 10/1993 |
| WO | WO9850773 | 11/1994 |
| WO | WO9535505 | 12/1995 |
| WO | WO 96/02830 | 2/1996 |
| WO | WO 96/26432 | 8/1996 |
| WO | WO 96/29629 | 9/1996 |
| WO | WO 96/38726 | 12/1996 |
| WO | WO 96/39937 | 12/1996 |
| WO | WO 97/07429 | 2/1997 |
| WO | WO 97/36681 | 10/1997 |
| WO | WO 97/41424 | 11/1997 |
| WO | WO 97/41425 | 11/1997 |
| WO | WO9823948 | 6/1998 |
| WO | WO99/40434 | 8/1999 |
| WO | WO00/52209 | 9/2000 |
| WO | WO00/53625 | 9/2000 |
| WO | WO00/54046 | 9/2000 |

OTHER PUBLICATIONS

Silzel et al. (1998). Mass–sensing, multianalyte microarray immunoassay with imaging detection. Clin. Chem. 44(9):2036–2043.*

Kricka (1998). Miniaturization of analytical systems. Clin. Chem. 44(9):2008–2014.*

(List continued on next page.)

Primary Examiner—Christopher L. Chin
(74) Attorney, Agent, or Firm—Townsend & Townsend Crew LLP

(57) ABSTRACT

Devices for the parallel, in vitro screening of biomolecular activity using miniaturized microfabricated devices are provided. The biomolecules immobilized on the surface of the devices of the present invention include proteins, polypeptides, polynucleotides, polysaccharides, phospolipids, and related unnatural polymers of biological relevance. These devices are useful drug development, functional proteomics and clinical diagnostics and are preferably used for the parallel screening of families of related proteins.

4 Claims, 8 Drawing Sheets

U.S. PATENT DOCUMENTS

| | | | |
|---|---|---|---|
| 5,079,600 A | 1/1992 | Schnur et al. ................. 357/4 |
| 5,096,807 A | 3/1992 | Leaback |
| 5,143,854 A | 9/1992 | Pirrung et al. .............. 436/518 |
| 5,154,808 A | 10/1992 | Miyasaka et al. |
| 5,160,597 A | 11/1992 | Colapicchioni et al. ..... 204/403 |
| 5,242,828 A | 9/1993 | Bergstrom et al. .......... 435/291 |
| 5,252,743 A | * 10/1993 | Barrett et al. ............... 548/303 |
| 5,294,369 A | 3/1994 | Shigekawa et al. ....... 252/313.1 |
| 5,296,114 A | * 3/1994 | Manz ...................... 204/180.1 |
| 5,304,487 A | * 4/1994 | Wilding et al. ............. 435/291 |
| 5,342,692 A | 8/1994 | Ribi .......................... 428/420 |
| 5,384,261 A | 1/1995 | Winkler et al. ............. 436/518 |
| 5,405,766 A | 4/1995 | Kallury et al. .............. 435/174 |
| 5,405,783 A | 4/1995 | Pirrung et al. .............. 436/518 |
| 5,412,087 A | 5/1995 | McGall et al. ............. 536/24.3 |
| 5,429,708 A | 7/1995 | Linford et al. ................ 216/66 |
| 5,441,876 A | 8/1995 | Singh |
| 5,445,934 A | 8/1995 | Fodor et al. .................... 435/6 |
| 5,472,881 A | 12/1995 | Beebe et al. .................. 436/94 |
| 5,510,270 A | 4/1996 | Fodor et al. ................. 436/518 |
| 5,512,131 A | 4/1996 | Kumar et al. ............. 156/655.1 |
| 5,512,492 A | 4/1996 | Herron et al. .............. 436/518 |
| 5,514,501 A | 5/1996 | Tarlov .......................... 430/5 |
| 5,520,787 A | 5/1996 | Hanagan et al. ............ 204/409 |
| 5,571,410 A | 11/1996 | Swedberg et al. ....... 210/198.2 |
| 5,593,838 A | 1/1997 | Zanzucchi et al. ............. 435/6 |
| 5,603,351 A | 2/1997 | Cherukuri et al. .......... 137/597 |
| 5,605,662 A | 2/1997 | Heller et al. ............... 422/68.1 |
| 5,620,850 A | * 4/1997 | Bamdad et al. ............. 530/300 |
| 5,622,826 A | 4/1997 | Varma .......................... 435/6 |
| 5,624,711 A | * 4/1997 | Sundberg et al. ........... 427/261 |
| 5,629,213 A | 5/1997 | Kornguth et al. ........... 436/518 |
| 5,635,358 A | 6/1997 | Wilding et al. .............. 435/7.2 |
| 5,637,469 A | 6/1997 | Wilding et al. ............ 435/7.21 |
| 5,677,195 A | 10/1997 | Winkler et al. ............. 436/518 |
| 5,677,196 A | 10/1997 | Herron et al. .............. 436/518 |
| 5,681,484 A | * 10/1997 | Zanzucchi et al. ............. 216/2 |
| 5,688,642 A | 11/1997 | Chrisey et al. ................ 435/6 |
| 5,700,642 A | 12/1997 | Monforte et al. .............. 435/6 |
| 5,719,060 A | 2/1998 | Hutchens et al. ........... 436/174 |
| 5,726,026 A | * 3/1998 | Wilding et al. ............ 435/7.21 |
| 5,731,152 A | 3/1998 | Maracas et al. .................. 3/98 |
| 5,744,305 A | 4/1998 | Fodor et al. .................... 435/6 |
| 5,766,908 A | 6/1998 | Klein et al. |
| 5,776,674 A | 7/1998 | Ulmer |
| 5,837,832 A | 11/1998 | Chee et al. |
| 5,843,767 A | 12/1998 | Beattie et al. |
| 5,849,208 A | 12/1998 | Hayes et al. |
| 5,858,188 A | * 1/1999 | Soane et al. ................. 204/454 |
| 5,861,242 A | 1/1999 | Chee et al. |
| 5,866,345 A | 2/1999 | Wilding et al. |
| 5,919,523 A | 7/1999 | Sundberg et al. |
| 5,925,552 A | 7/1999 | Keogh et al. |
| 5,928,880 A | 7/1999 | Wilding et al. |
| 5,942,443 A | * 8/1999 | Parce et al. ................. 436/514 |
| 6,046,056 A | 4/2000 | Parce et al. |
| 6,048,709 A | 4/2000 | Falb |

OTHER PUBLICATIONS

Ekins (1998). Ligand assays: from electrophoresis to miniaturized microarrays. Clin. Chem. 44(9):2015–2030.*

Jones et al. (1998). Microminiaturized immunoassays using atomic force microscopy and compositionally patterned antigen arrays. Anal. Chem. 70(7):1223–1241.*

Dzgoev et al. (1996). Microformat imaging ELISA for pesticide determination. Anal. Chem. 68(19):3364–3369.*

Rowe et al. (1999). Array biosensor for simultaneous identification of bacterial, viral and protein analytes. Anal. Chem. 71(17):3846–3852.*

Elkins et al. (1991). Multianalyte microspot immunoassay–microanalytical "compact disk" of the future. Clin. Chem. 37(11):1955–1967.*

Becker et al., "Fabrication of microstructures with high aspect ratios and great structural heights by synchrotron radiation lithography, galvanoforming, and plastic moulding (LIGA process)," *Microelectronic Engineering,* 4:35–56 (1986).

Becker et al., "Production of separation–nozzle systems for uranium enrichment by a combination of x–ray lithography and galvanoplastics," *Naturwissenschaften,* 69:520–523 (1982).

Cload et al., "Development of improved tRNAs for in vitro biosynthesis of proteins containing unnatural amino acids," *Chemistry & Biology,* 3:1033–1038 (1996).

Condra et al., "In vivo emergence of HIV–1 variants resistant to multiple protease inhibitors," *Nature,* 374:569–571 (1995).

Dammer et al., "Specific antigen/antibody interactions measured by force microscopy," *Biophysical Journal,* 70:2437–2441 (1996).

Dawson et al., "Peptide–derived self–assembled monolayers: adsorption of N–stearoyl I–Cysteine Methyl Ester on Gold," *Journal of Molecular Recognition,* 10:18–25 (1997).

Duschl et al., "Surface engineering: optimization of antigen presentation in self–assembled monolayers," *Biophysical Journal,* 70:1985–1995 (1996).

Ellman et al., "Biosynthetic method for introducing unnatural amino acids site–specifically into proteins," *Methods in Enzymology,* 202:301–336 (1991).

Geoghegan et al., "Fluorescence–based continuous assay for the aspartyl protease of human immunodeficiency virus–1," *FEBS,* 262:119–122 (1990).

Hegner et al., "Ultralarge atomically flat template–stripped Au surfaces for scanning probe microscopy," *Surface Science,* 291:39–46 (1993).

Hegner et al., "Immobilizing DNA on gold via thiol–modification for atomic force microscopy imaging in buffer solutions," *FEBS,* 336(3):452–456 (1993).

Hegner et al., "Modified DNA immobilized on bioreactive self–assembled monolayer on gold for dynamic force microscopy imaging in aqueous buffer solution," *J. Vac. Sci. Technol. B,* 14(2):1418–1421 (1996).

Ho et al., "Characterization of human immunodeficiency virus type 1 variants with increased resistance to a $C_2$–symmetric protease inhibitor," *Journal of Virology,* 68:2016–2020 (1994).

Hochuli et al., "Genetic approach to facilitate purification of recombinant proteins with a novel metal chelate adsorbent," *Biotechnology,* 6:1321–1325 (1988).

Kaplan et al., "Selection of multiple human immunodeficiency virus type 1 variants that encode viral proteases with decreased sensitivity to an inhibitor of the viral protease," *Proc. Natl. Acad. Sci. USA,* 91:5597–5601 (1994).

Korant et al., "The HIV protease and therapies for aids," *Advances in Experimental Medicine and Biology,* 421:279–284 (1997).

Linford et al., "Alkyl monolayers on silicon prepared from 1–alkenes and hydrogen–terminated silicon," *J. Am. Chem. Soc.,* 117:3145–3155 (1995).

Loeb et al., "Complete mutagenesis of the HIV–1 protease," *Nature,* 340:397–400 (1989).

Louis et al., "Autoprocessing of the HIV–1 protease using purified wild–type and mutated fusion proteins expressed at high levels in *Escherichia coli,*" *Eur. J. Biochem.,* 199:361–369 (1991).

Mrksich et al., "Controlling cell attachment on contoured surfaces with self–assembled monolayers of alkanethiolates on gold," *Proc. Natl. Acad. Sci. USA,* 93:10775–10778 (1996).

Moore et al., "Peptide substrates and inhibitors of the HIV–1 protease," *Biochemical and Biophysical Research Communications,* 159:420–425 (1989).

Nock, "Reversible, site–specific immobilization of polyarginine–tagged fusio proteins on mica surfaces," *FEBS,* 414:233–238 (1997).

Noren et al., "A general method for site–specific incorporation of unnatural amino acids into proteins," *Science,* 244:182–188 (1989).

Prime et al., "Self–assembled organic monolayers: model systems for studying absorption of proteins at surfaces," *Science,* 252:1164–1167 (1991).

Roberts et al., "Rational design of peptide–based HIV proteinase inhibitors," *Science,* 248:358–361 (1990).

Schock et al., "Mutational anatomy of an HIV–1 protease variant conferring cross–resistance to protease inhibitors in clinical trials," *The Journal of Biological Chemistry,* 271:31957–31963 (1996).

Singhvi et al., "Engineering cell shape and function," *Science,* 264:696–698 (1994).

Skalka, "Retroviral proteases: first glimpses at the anatomy of a processing machine," *Cell,* 56:911–913 (1989).

Sundberg et al., "Spatially–addressable immobilization of macromolecules on solid supports," *J. Am. Chem. Soc.,* 117:12050–12057 (1995).

Wagner et al., "ω–functionalized self–assembled monolayers chemisorbed on ultraflat Au(111) surfaces for biological scanning probe microscopy in aqueous buffers," *J. Vac. Sci. Technol. B,* 14(2):1466–1471 (1996).

Wagner et al., "Formation and in Situ modification of monolayers chemisorbed on ultraflat template–stripped gold surfaces," *Langmuir,* 11(10):3867–3875 (1995).

Wagner et al., "Bioreactive self–assembled monolayers on hydrogen–passivated Si(111) as a new class of atomically flat substrates for biological scanning probe microscopy," *Journal of Structural Biology,* 119:189–201 (1997).

Wagner et al., "Covalent immobilization of native bimolecules onto Au(111) via N–hydroxysuccinimide ester functionalized self–assembled monolayers for scanning probe microscopy," *Biophysical Journal,* 70:2052–2066 (1996).

Weiner et al., "Site–directed mutagenesis of double–stranded DNA by the polymerase chain reaction," *Gene,* 151:119–123 (1994).

Wondrak et al., "Influence of flanking sequences on the dimer stability of human immunodeficiency virus type 1 protease," *Biochemistry,* 35:12957–12962 (1996).

Wu et al., "Structural basis for specificity of retroviral proteases," *Biochemistry,* 37:4518–4526 (1998).

Cha et al. "Expression of Fused Protein, Human Interleukin–2 and Green Fluorescent Protein, in Insect Larvae . . . " Ann. Meeting of The Am. Inst. Chem. Eng., Los Angeles (11/97).

Colliod et al. "Oriented and Covalent Immobilization of Target Molecules to Solid Supports: Synthesis and Application of a Light–Activatable and Thiol–Reactive Cross–Linking Reagent" *Bioconjugate Chem.* 4:528–536 (1993).

Ekins et al. "Multianalyte Microspote Immunoassay–Microanalytical "Compact Disk" of the Future" Clin. Chem. 37(11):1955–1967 (1991).

Jacobson et al. "Fused Quartz Substrates for Microchip Electrophoresis" Anal. Chem. 67:2059–2063 (Jul. 1995).

Kemeny "Enzyme–linked immunoassays" In Immuno Chemistry 1 (eds Johnstone and Turner) p 147–175 (11/97).

Lemmo et al. "Characterization of an Inkjet Chemical Microdispensor for Combinatorial Library Synthesis" Anal. Chem. 69:543:551 (1997).

Marks et al. "By–passing Immunication—Human Antibodies from V–gene Libraries Displayed on Phage" J. Mol. Biol. 222:581–597 (1991).

Martynova et al. "Fabricating of Plastic Microfluid Channels by Imprinting Methods" Anal. Chem. 69:4783–4789 (1997).

Mauracher et al. "Reduction of rubella ELISA background using heat denatured sample buffer" J. Immun. Meth. 145:251–254 (1991).

Pale–Grosdemange et al. "Formation of Self–Assembled Monolayers by Chemisorption of Derivatives of Oligo (ethylene glycol) of Structure $HS(CH_2)_{11}(OCH_2CH_2)_mOH$ on Gold" J. Am. Chem. Soc. 113(1) 12–20 (1991).

Patent Abstract, Patent abstract of Japan (Fuji Film Co Ltd.), Patent Abstracts of Japan, v15(34) (c–0799) Jan. 1991 & JP 02 272081 A (11/90).

Sigal et al. "A Self–Assembled Monolayer for the Binding and Study of Histidine–Tagged Proteins by Surface Plasmon Resonance", Anal. Chem. 68:490–497 (1996).

Steinnicke et al. Biochemical Characteristics of Caspases–3, –6, –7, and –8 J. Biol. Chem. 272:25719–25723 (1997).

Talanian et al. "Substrate Specificities of Caspase Family Proteases", J. Biol. Chem. 272:9677–9682 (1997).

Thornberry, Nancy A. "Interleukin–1beta Converting Enzyme", Meth. In Enzymology 244:615–631 (1994).

Villa et al. "Caspases and caspase inhibitors", TIBS 22:388–393 (1997).

Wilson et al. "Structure and mechanism of interleukin–1beta converting enzyme" Nature 370:270–275 (1994).

\* cited by examiner

SEQUENCE LISTING

<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: histidine
      tag

<400> SEQUENCE: 1

His His His His His His
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: lysine tag

<400> SEQUENCE: 2

Lys Lys Lys Lys Lys Lys
 1               5

<210> SEQ ID NO 3
<211> LENGTH: 8
<212> TYPE: PRT
<213> ORGANISM: Artificial Sequence
<220> FEATURE:
<221> NAME/KEY: MOD_RES
<222> LOCATION: (1)
<223> OTHER INFORMATION: N-dansyl
<220> FEATURE:
<223> OTHER INFORMATION: Description of Artificial Sequence: labeled
      peptide substrate of HIV protease

<400> SEQUENCE: 3

Ser Gln Asn Tyr Pro Ile Val Trp
 1               5

MICRODEVICES FOR SCREENING BIOMOLECULES

This application is a continuation-in-part application of co-pending application Ser. No. 09/115,397, filed Jul. 14, 1998, which is incorporated herein by reference in its entirety.

BACKGROUND OF THE INVENTION a) Field of the Invention

The present invention relates generally to microdevices and methods of using those devices for the parallel, in vitro screening of a plurality of biomolecule-analyte interactions. More specifically, the present invention relates to use of the devices for drug development, functional proteomics, and clinical diagnostics.

b) Description of Related Art

A vast number of new drug targets are now being identified using a combination of genomics, bioinformatics, genetics, and high-throughput biochemistry. Genomics provides information on the genetic composition and the activity of an organism's genes. Bioinfornatics uses computer algorithms to recognize and predict structural patterns in DNA and proteins, defining families of related genes and proteins. The information gained from the combination of these approaches is expected to greatly boost the number of drug targets (usually, proteins).

The number of chemical compounds available for screening as potential drugs is also growing dramatically due to recent advances in combinatorial chemistry, the production of large numbers of organic compounds through rapid parallel and automated synthesis. The compounds produced in the combinatorial libraries being generated will far outnumber those compounds being prepared by traditional, manual means, natural product extracts, or those in the historical compound files of large pharmaceutical companies.

Both the rapid increase of new drug targets and the availability of vast libraries of chemical compounds creates an enormous demand for new technologies which improve the screening process. Current technological approaches which attempt to address this need include multiwell-plate based screening systems, cell-based screening systems, microfluidics-based screening systems, and screening of soluble targets against solid-phase synthesized drug components.

Automated multiwell formats are the best developed high-throughput screening systems. Automated 96-well plate-based screening systems are the most widely used. The current trend in plate based screening systems is to reduce the volume of the reaction wells further, thereby increasing the density of the wells per plate (96-well to 384- and 1536-well per plate). The reduction in reaction volumes results in increased throughput, dramatically decreased bioreagent costs, and a decrease in the number of plates which need to be managed by automation.

However, although increases in well numbers per plate are desirable for high throughput efficiency, the use of volumes smaller than 1 microliter in the well format generates significant problems with evaporation, dispensing times, protein inactivation, and assay adaptation. Proteins are very sensitive to the physical and chemical properties of the reaction chamber surfaces. Proteins are prone to denaturation at the liquid/solid and liquid/air interfaces. Miniaturization of assays to volumes smaller than 1 microliter increases the surface to volume ratio substantially. (Changing volumes from 1 microliter to 10 nanoliter increases the surface ratio by 460%, leading to increased protein inactivation.) Furthermore, solutions of submicroliter volumes evaporate rapidly, within seconds to a few minutes, when in contact with air. Maintaining microscopic volumes in open systems is therefore very difficult.

Other types of high-throughput assays, such as miniaturized cell-based assays are also being developed. Miniaturized cell-based assays have the potential to generate screening data of superior quality and accuracy, due to their in vivo nature. However, the interaction of drug compounds with proteins other than the desired targets is a serious problem related to this approach which leads to a high rate of false positive results.

Microfluidics-based screening systems that measure in vitro reactions in solution make use of ten to several-hundred micrometer wide channels. Micropumps, electroosmotic flow, integrated valves and mixing devices control liquid movement through the channel network. Microfluidic networks prevent evaporation but, due to the large surface to volume ratio, result in significant protein inactivation. The successful use of microfluidic networks in biomolecule screening remains to be shown.

Drug screening of soluble targets against solid-phase synthesized drug components is intrinsically limited. The surfaces required for solid state organic synthesis are chemically diverse and often cause the inactivation or non-specific binding of proteins, leading to a high rate of false-positive results. Furthermore, the chemical diversity of drug compounds is limited by the combinatorial synthesis approach that is used to generate the compounds at the interface. Another major disadvantage of this approach stems from the limited accessibility of the binding site of the soluble target protein to the immobilized drug candidates.

Miniaturized DNA chip technologies have been developed (for example, see U.S. Pat. Nos. 5,412,087, 5,445,934 and 5,744,305) and are currently being exploited for nucleic acid hybridization assays. However, DNA biochip technology is not transferable to protein assays because the chemistries and materials used for DNA biochips are not readily transferable to use with proteins. Nucleic acids withstand temperatures up to 100° C., can be dried and re-hydrated without loss of activity, and can be bound directly to organic adhesion layers supported by materials such as glass while maintaining their activity. In contrast, proteins must remain hydrated, kept at ambient temperatures, and are very sensitive to the physical and chemical properties of the support materials. Therefore, maintaining protein activity at the liquid-solid interface requires entirely different immobilization strategies than those used for nucleic acids. Additionally, the proper orientation of the protein at the interface is desirable to ensure accessibility of their active sites with interacting molecules. With miniaturization of the chip and decreased feature sizes the ratio of accessible to non-accessible antibodies becomes increasingly relevant.

In addition to the goal of achieving high-throughput screening of compounds against targets to identify potential drug leads, researchers also need to be able to identify highly specific lead compounds early in the drug discovery process. Analyzing a multitude of members of a protein family or forms of a polymorphic protein in parallel (multitarget screening) enables quick identification of highly specific lead compounds. Proteins within a structural family share similar binding sites and catalytic mechanisms. Often, a compound that effectively interferes with the activity of one family member also interferes with other members of the same family. Using standard technology to discover such additional interactions requires a tremendous effort in time and costs and as a consequence is simply not done.

However, cross-reactivity of a drug with related proteins can be the cause of low efficacy or even side effects in patients. For instance, AZT, a major treatment for AIDS, blocks not only viral polymerases, but also human polymerases, causing deleterious side effects. Cross-reactivity with closely related proteins is also a problem with nonsteroidal anti-inflammatory drugs (NSAIDs) and aspirin. These drugs inhibit cyclooxygenase-2, an enzyme which promotes pain and inflammation. However, the same drugs also strongly inhibit a related enzyme, cyclooxygenase-1, that is responsible for keeping the stomach lining and kidneys healthy, leading to common side-effects including stomach irritation.

The miniaturized, parallel screening of a plurality of protein interactions is also useful and necessary for a number of applications beyond high-throughput drug screening. For instance, the function of newly discovered proteins could be assayed effectively in a parallel format with a plurality of potential ligands or potential substrates of known protein families. Also, miniaturized diagnostic devices which allow for the analysis of a plurality of analytes by binding the analytes to proteins such as antibodies would be desirable.

For the foregoing reasons, there is a need for a miniaturized device and methods of using the device for the parallel, in vitro, screening of a plurality of biomolecular interactions, especially the interactions of proteins with analytes or other proteins.

SUMMARY OF THE INVENTION

The present invention is directed to a device and methods of use of the device that satisfy the need for the parallel, in vitro, screening of a plurality of biomolecular interactions, especially the interactions of proteins with analytes or other proteins.

One embodiment of the present invention provides a device for analyzing components of a fluid sample, comprising a plurality of noncontiguous reactive sites. Each of the reactive sites comprises a substrate, an organic thinfilm chermisorbed or physisorbed on a portion of a surface of the substrate, and a biological moiety immobilized on the organic thinfilm, wherein each of the reactive sites may independently react with a component of the fluid sample and are separated from each other by a region of the substrate that is free of organic thinfilm.

In a particularly preferred embodiment of the device, each of the reactive sites on the device of the invention is in a microchannel oriented parallel to microchannels of other reactive sites on the device, where the microchannels are microfabricated into or onto the substrate.

An alternative embodiment of the invention provides a device for analyzing components of a fluid sample that comprises a substrate, a plurality of parallel microchannels microfabricated into or onto said substrate, and a biological moiety immobilized within at least one of the parallel microchannels in such a way that the biological moiety may interact with a component of the fluid sample. In a preferred embodiment, the biological moiety is a protein.

Methods of using the devices of the invention are also provided by the present invention. In one embodiment, the invention provides for a method of screening a plurality of biological moieties in parallel for their ability to interact with a component of a fluid sample. This method comprises first delivering the fluid sample to the reactive sites of the invention device, where each of the different biological moieties is immobilized on a different reactive site of the device and detecting, either directly or indirectly, for the interaction of the component with the immobilized biological moiety at each reactive site. The interaction being assayed may be a binding interaction, catalysis, or translocation by a membrane protein through a lipid bilayer.

In an alternative embodiment of the invention, the device of the invention is used to screen a plurality of components, each in separate fluid samples, for their ability to interact with a biological moiety. The method of this embodiment comprises first delivering each of the different fluid samples to separate reactive sites of the invention device, wherein the separate reactive sites of the device each comprise the immobilized biological moiety. The next step comprises detecting, either directly or indirectly, for the interaction of the immobilized biological moiety at each reactive site with the component delivered to that reactive site. Again, the interaction being assayed may be a binding interaction, catalysis, or translocation by a membrane protein through a lipid bilayer.

In another embodiment of the present invention, a similar method is used to screen a fluid sample for the presence or amount of a plurality of analytes (in parallel). This method has potential applications in diagnostics. The method comprises delivering the fluid sample to a plurality of reactive sites on the invention device, wherein each of the reactive sites comprises an immobilized biological moiety which can either react, bind, or otherwise interact with at one of said plurality of analytes. The method also comprises a final step of detecting for the interaction of the analyte with the immobilized biological moiety of each reactive site.

In another embodiment of the invention, the device may also be used to screen a plurality of binding candidates in parallel for their ability to bind to a biological moiety. In the method of this embodiment, different fluid samples, each containing a different binding candidate (or a different mixture of binding candidates) to be tested, are delivered separate reactive sites of the invention device, wherein the separate reactive sites each comprise the immobilized biological moiety. The next step of the method comprises detecting, either directly or indirectly, for the presence or amount of the binding candidate.

The present invention also provides for methods of determining in parallel whether or not each of a plurality of proteins belong to a certain protein family based on either binding to a common ligand or reactivity with a common substrate. These methods involve delivering a fluid sample comprising a ligand or substrate of a known protein family to the reactive sites of the invention device which each contain one of the different proteins to be assayed and then detecting, either directly or indirectly, for binding or reaction with the known ligand that is characteristic of the protein family.

DETAILED DESCRIPTION OF THE INVENTION

Figure 1:
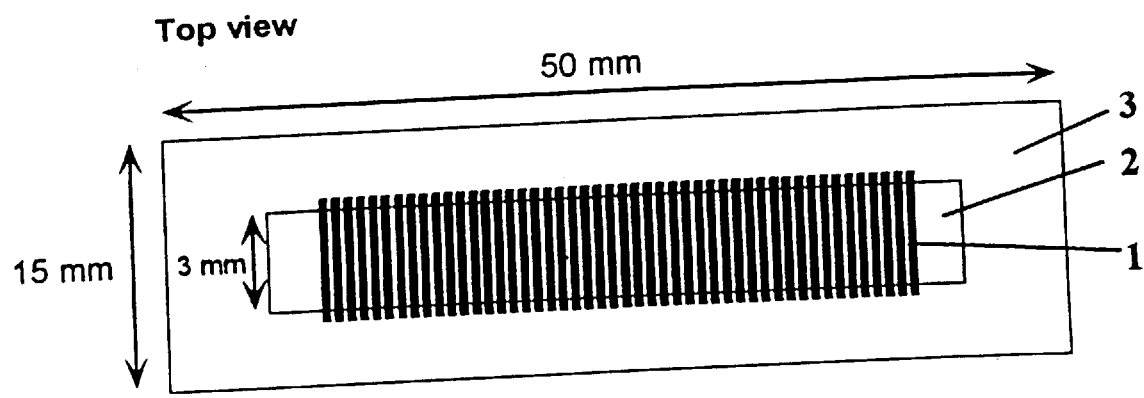
FIG. 1 shows the top view of a covered microchannel array device.

A variety of devices and methods useful for drug development, proteomics, and, clinical diagnostics are provided by the present invention.

(a) Definitions

The terms "biological moiety" and "biomolecule" are used interchangeably and each refer to any entity that either has, or is suspected of having, a physiological function. The biological moiety may be a single molecule or may be a macromolecular complex. One example of a biological moiety is a polynucleotide. A preferred biological moiety is a protein. The protein may be any intracellular or an extracellular protein, including any membrane protein or secreted protein. Other possible biological moieties include small molecule compounds which can act as inhibitors of enzymes or which can bind other biomolecules. For instance, a biological moiety may optionally be a protein-capture agent.

The term "polynucleotide" means a deoxyribonucleotide or ribonucleotide polymer in either single- or double-stranded form, and unless otherwise limited, encompasses known analogs of natural nucleotides that can function in a manner similar to naturally occurring nucleotides. The polynucleotide may be obtained from a natural source or produced in vitro or in vivo by enzymatic or chemical synthesis. No distinction is made herein between a nucleic acid, a polynucleotide, and an oligonucleotide. Preferably the polynucleotide comprises at least about 16 nucleotides.

A "protein" means a polymer of amino acid residues linked together by peptide bonds. The term, as used herein, refers to proteins, polypeptides, and peptides of any size, structure, or function. Typically, however, a protein will be at least about six amino acids long. Preferably, if the protein is a short peptide, it will be at least about 10 amino acid residues long. A protein may be naturally occurring, recombinant, or synthetic, or any combination of these. A protein may also be just a fragment of a naturally occurring protein or peptide. A protein may be a single molecule or may be a multi-molecular complex. The term protein may also apply to amino acid polymers in which one or more amino acid residues is an artificial chemical analogue of a corresponding naturally occurring amino acid. An amino acid polymer in which one or more amino acid residues is an "unnatural" amino acid, not corresponding to any naturally occurring amino acid, is also encompassed by the use of the term "protein" herein.

A "fragment of a protein" means a protein which is a portion of another protein. For instance, fragments of a proteins may be polypeptides obtained by doing a digest of full-length protein isolated from cultured cells. A fragment of a protein will typically comprise at least six amino acids. More typically, the fragment will comprise at least ten amino acids. Preferably, the fragment comprises at least about 16 amino acids.

The term "antibody" means an immunoglobulin, whether natural or wholly or partially synthetically produced. All derivatives thereof which maintain specific binding ability are also included in the term. The term also covers any protein having a binding domain which is homologous or largely homologous to an immunoglobulin binding domain, including chimeric and humanized antibodies. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. Derivatives of the IgG class, however, are preferred in the present invention.

The term "antibody fragment" refers to any derivative of an antibody which is less than full-length. Preferably, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

Single-chain Fvs (scFvs) are recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility.

"Diabodies" are dimeric scFvs. The components of diabodies typically have shorter peptide linkers than most scFvs and they show a preference for associating as dimers.

An "Fv" fragment is an antibody fragment which consists of one $V_H$ and one $V_L$ domain held together by noncovalent interactions. The term "dsFv" is used herein to refer to an Fv with an engineered intermolecular disulfide bond to stabilize the $V_H$-$V_L$ pair.

A "F(ab')$_2$" fragment is an antibody fragment essentially equivalent to that obtained from immunoglobulins (typically IgG) by digestion with an enzyme pepsin at pH 4.0–4.5. The fragment may be recombinantly produced.

A "Fab'" fragment is an antibody fragment essentially equivalent to that obtained by reduction of the disulfide bridge or bridges joining the two heavy chain pieces in the F(ab')$_2$ fragment. The Fab' fragment may be recombinantly produced.

A "Fab" fragment is an antibody fragment essentially equivalent to that obtained by digestion of immunoglobulins (typically IgG) with the enzyme papain. The Fab fragment may be recombinantly produced. The heavy chain segment of the Fab fragment is the Fd piece.

The term "protein-capture agent" means a molecule or a multi-molecular complex which can bind a protein to itself Protein-capture agents preferably bind their binding partners in a substantially specific manner. Protein-capture agents with a dissociation constant ($K_D$) of less than about $10^{-6}$ are preferred. Antibodies or antibody fragments are highly suitable as protein-capture agents. Antigens may also serve as protein-capture agents, since they are capable of binding antibodies. A receptor which binds a protein ligand is another example of a possible protein-capture agent. Protein-capture agents are understood not to be limited to agents which only interact with their binding partners through noncovalent interactions. Protein-capture agents may also optionally become covalently attached to the proteins which they bind. For instance, the protein-capture agent may be photocrosslinked to its binding partner following binding.

The term "binding partner" means a protein which is bound by a particular protein-capture agent, preferably in a substantially specific manner. In some cases, the binding partner may be the protein normally bound in vivo by a protein which is a protein-capture agent. In other embodiments, however, the binding partner may be the protein or peptide on which the protein-capture agent was selected (through in vitro or in vivo selection) or raised (as in the case of antibodies). A binding partner may be shared by more than one protein-capture agent. For instance, a binding partner which is bound by a variety of polyclonal antibodies may bear a number of different epitopes. One protein-capture agent may also bind to a multitude of binding partners (for instance, if the binding partners share the same epitope), "Conditions suitable for protein binding" means those conditions (in terms of salt concentration, pH, detergent, protein concentration, temperature, etc.) which allow for binding to occur between a protein-capture agent and its binding partner in solution. Preferably, the conditions are not so lenient that a significant amount of nonspecific protein binding occurs.

A "body fluid" may be any liquid substance extracted, excreted, or secreted from an organism or tissue of an organism. The body fluid need not necessarily contain cells. Body fluids of relevance to the present invention include, but are not limited to, whole blood, serum, urine, plasma, cerebral spinal fluid, tears, sinovial fluid, and amniotic fluid.

The term "substrate" refers to the bulk, underlying, and core material of the devices of the invention.

The terms "micromachining" and "microfabrication" both refer to any number of techniques which are useful in the generation of microstructures (structures with feature sizes of sub-millimeter scale). Such technologies include, but are not limited to, laser ablation, electrodeposition, physical and chemical vapor deposition, photolithography, and wet chemical and dry etching. Related technologies such as injection molding and LIGA (x-ray lithography, electrodeposition, and molding) are also included. Most of these techniques were originally developed for use in semiconductors, microelectronics, and Micro-ElectroMechanical Systems (MEMS) but are applicable to the present invention as well.

The term "coating" means a layer that is either naturally or synthetically formed on or applied to the surface of the substrate. For instance, exposure of a substrate, such as silicon, to air results in oxidation of the exposed surface. In the case of a substrate made of silicon, a silicon oxide coating is formed on the surface upon exposure to air. In other instances, the coating is not derived from the substrate and may be placed upon the surface via mechanical, physical, electrical, or chemical means. An example of this type of coating would be a metal coating that is applied to a silicon or polymer substrate or a silicon nitride coating that is applied to a silicon substrate. Although a coating may be of any thickness, typically the coating has a thickness smaller than that of the substrate.

An "interlayer" is an additional coating or layer that is positioned between the first coating and the substrate. Multiple interlayers may optionally be used together. The primary purpose of a typical interlayer is to aid adhesion between the first coating and the substrate. One such example is the use of a titanium or chromium interlayer to help adhere a gold coating to a silicon or glass surface. However, other possible functions of an interlayer are also anticipated. For instance, some interlayers may perform a role in the detection system of the device (such as a semiconductor or metal layer between a nonconductive substrate and a nonconductive coating).

An "organic thinfilm" is a thin layer of organic molecules which has been applied to a substrate or to a coating on a substrate if present. Typically, an organic thinfilm is less than about 20 nm thick. Optionally, an organic thinfilm may be less than about 10 nm thick. An organic thinfilm may be disordered or ordered. For instance, an organic thinfilm can be amorphous (such as a chemisorbed or spin-coated polymer) or highly organized (such as a Langmuir-Blodgett film or self-assembled monolayer). An organic thinfilm may be heterogeneous or homogeneous. Organic thinfilms which are monolayers are preferred. A lipid bilayer or monolayer is a preferred organic thinfilm. Optionally, the organic thinfilm may comprise a combination of more than one form of organic thinfilm. For instance, an organic thinfilm may comprise a lipid bilayer on top of a self-assembled monolayer. A hydrogel may also compose an organic thinfilm. The organic thinfilm will typically have functionalities exposed on its surface which serve to enhance the surface conditions of a substrate or the coating on a substrate in any of a number of ways. For instance, exposed functionalities of the organic thinfilm are typically useful in the binding or covalent immobilization of the biological moieties to the device. Alternatively, the organic thinfilm may bear functional groups (such as polyethylene glycol (PEG)) which reduce the non-specific binding of biomolecules and other analytes to the surface. Other exposed functionalities serve to tether the thinfilm to the surface of the substrate or the coating. Particular functionalities of the organic thinfilm may also be designed to enable certain detection techniques to be used with the surface. Alternatively, the organic thinfilm may serve the purpose of preventing inactivation of a biological moiety immobilized on the device from occurring upon contact with the surface of a substrate or a coating on the surface of a substrate.

A "monolayer" is a single-molecule thick organic thinfilm. A monolayer may be disordered or ordered. A monolayer may optionally be a polymeric compound, such as a polynonionic polymer, a polyionic polymer, or a block-copolymer. For instance, the monolayer may be composed of a poly(amino acid) such as polylysine. A monolayer which is a self-assembled monolayer, however, is most preferred. One face of the self-assembled monolayer is typically composed of chemical functionalities on the termini of the organic molecules that are chemisorbed or physisorbed onto the surface of the substrate or the coating, if present, on the substrate. Examples of suitable functionalities of monolayers include the positively charged amino groups of poly-L-lysine for use on negatively charged surfaces and thiols for use on gold surfaces. Typically, the other face of the self-assembled monolayer is exposed and may bear any number of chemical functionalities (end groups). Preferably, the molecules of the self-assembled monolayer are highly ordered.

A "self-assembled monolayer" is a monolayer which is created by the spontaneous assembly of molecules. The self-assembled monolayer may be ordered, disordered, or exhibit short- to long-range order.

An "affinity tag" is a functional moiety capable of directly or indirectly immobilizing a biological moiety onto an exposed functionality of the organic thinfilm. Preferably, the affinity tag enables the site-specific immobilization and thus enhances orientation of the biological moiety onto the organic thinfilm. In some cases, the affinity tag may be a simple chemical functional group. Other possibilities include amino acids, poly(amino acid) tags, or full-length proteins. Still other possibilities include carbohydrates and nucleic acids. For instance, the affinity tag may be a polynucleotide which hybridizes to another polynucleotide serving as a functional group on the organic thinfilm or another polynucleotide serving as an adaptor. The affinity tag may also be a synthetic chemical moiety. If the organic thinfilm of each of the sites comprises a lipid bilayer or monolayer, then a membrane anchor is a suitable affinity tag. The affinity tag may be covalently or noncovalently attached to the biological moiety. For instance, if the affinity tag is covalently attached to a biological moiety which is a protein, it may be attached via chemical conjugation or as a fusion protein. The affinity tag may also be attached to the biological moiety via a cleavable linkage. Alternatively, the affinity tag may not be directly in contact with the biological moiety. The affinity tag may instead be separated from the biological moiety by an adaptor. The affinity tag may immobilize the biological moiety to the organic thinfilm either through noncovalent interactions or through a covalent linkage.

An "adaptor", for purposes of this invention, is any entity that links an affinity tag to the immobilized biological moiety of the device. The adaptor may be, but need not necessarily be, a discrete molecule that is noncovalently attached to both the affinity tag and the biological moiety. The adaptor can instead be covalently attached to the affinity tag or the biological moiety or both (via chemical conjugation or as a fusion protein, for instance). Proteins such as full-length proteins, polypeptides, or peptides are typical adaptors. Other possible adaptors include carbohydrates and nucleic acids.

The term "fusion protein" refers to a protein composed of two or more polypeptides that, although typically unjoined in their native state, are joined by their respective amino and carboxyl termini through a peptide linkage to form a single continuous polypeptide. It is understood that the two or more polypeptide components can either be directly joined or indirectly joined through a peptide linker/spacer.

The term "normal physiological condition" means conditions that are typical inside a living organism or a cell. While it is recognized that some organs or organisms provide extreme conditions, the intra-organismal and intra-cellular environment normally varies around pH 7 (i.e., from pH 6.5 to pH 7.5), contains water as the predominant solvent, and exists at a temperature above 0° C. and below 50° C. It will be recognized that the concentration of various salts depends on the organ, organism, cell, or cellular compartment used as a reference.

"Proteomics" means the study of or the characterization of either the proteome or some fraction of the proteome. The "proteome" is the total collection of the intracellular proteins of a cell or population of cells and the proteins secreted by the cell or population of cells. This characterization most typically includes measurements of the presence, and usually quantity, of the proteins which have been expressed by a cell. The function, structural characteristics (such as post translational modification), and location within the cell of the proteins may also be studied. "Functional proteomics" refers to the study of the functional characteristics, activity level, and structural characteristics of the protein expression products of a cell or population of cells.

(b) The Devices of the Invention

In one aspect, the present invention provides a device for analyzing components of a fluid sample. This device comprises a plurality of noncontiguous reactive sites, each of which comprises the following: a substrate; an organic thinfilm chemisorbed or physisorbed on a portion of a surface of the substrate; and a biological moiety immobilized on the organic thinfilm, wherein each of the sites may independently react with a component of the fluid sample and are separated from each other by a region of the substrate that is free of the organic thinfilm.

In a preferred embodiment, the device comprises at least about 10 reactive sites. In an especially preferred embodiment, the device comprises at least about 100 reactive sites.

In a preferred embodiment of the present invention the device comprises a micromachined or microfabricated device. The device is optionally a microdevice with dimensions on the millimeter to centimeter scale.

In a preferred embodiment of the invention, each of the reactive sites of the device is in a microchannel oriented parallel to microchannels of other reactive sites on the device. The microchannels of such a device have optionally been microfabricated or micromachined into or onto the substrate of the device. A reactive site may optionally cover the entire interior surface of the microchannel or alternatively, only a portion of the interior surface of the microchannel.

In another embodiment, the invention provides a device for analyzing components of a fluid sample which comprises a substrate, a plurality of parallel microchannels microfabricated into or onto the substrate, and a biological moiety immobilized within at least one of the parallel microchannels, wherein the biological moiety may interact with a component of the fluid sample. Preferably, a number of parallel microchannels will comprise immobilized biological moieties. It is also preferred that the immobilized biological moiety of each microchannel be immobilized on an organic thinfilm on at least a portion of the inner surface of the microchannel.

FIG. 1 illustrates one embodiment of the invention showing an array of microchannels 1 that have been fabricated into a bulk substrate material. In the particular device shown, forty-eight parallel microchannels 1 have been microfabricated into a substrate 3. A glass cover 2 covers a portion of the microchannel array.

In one embodiment of the invention, the device comprises at least 2 parallel microchannel reactive sites. In another embodiment of the invention, the device comprises at least 10 parallel microchannel reactive sites. In a preferred embodiment of the invention, the device comprises at least 100 parallel microchannel reactive sites. In a particularly preferred embodiment, the device comprises from about 100 to about 500 parallel microchannels. The microchannels are typically separated from one another by from about 10 μm to about 5 μmm. The device may optionally comprise from about 2 to about 500 parallel microchannels per cm² of substrate.

The dimensions of the microchannels may vary. However, in preferred embodiments the scale is small enough so as to only require minute fluid sample volumes. The width and depth of each microchannel of the invention device is typically between about 10 μm and about 500 μm. In a preferred embodiment of the device, the width and depth of each microchannel is between about 50 and 200 μm. The length of each microchannel is from about 1 to about 20 mm in length. In a preferred embodiment, the length of each microchannel is from about 2 to about 8 mm long. Any channel cross-section geometry (trapezoidal, rectangular, v-shaped, semicircular, etc.) may be employed in the device. The geometry is determined by the type of microfabrication or micromachining process used to generate the microchannels, as is known in the art. Trapezoidal or rectangular cross-section geometries are preferred for the microchannels, since they readily accommodate standard fluorescence detection methods.

Numerous different materials may be used as the substrate of the invention device. The substrate may be organic or inorganic, biological or non-biological, or any combination of these materials. The substrate can optionally be transparent or translucent. Substrates suitable for micromachining or microfabrication are preferred. The substrate of the invention can optionally comprise a material selected from a group consisting of silicon, silica, quartz, glass, controlled pore glass, carbon, alumina, titania, tantalum oxide, germanium, silicon nitride, zeolites, and gallium arsenide. Many metals such as gold, platinum, aluminum, copper, titanium, and their alloys are also options for substrates. In addition, many ceramics and polymers may also be used as substrates. Polymers which may be used as substrates include, but are not limited to, the following: polystyrene; poly(tetra)fluoroethylene (PTFE); polyvinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PMI); polyalkenesulfone (PAS); polypropylene; polyethylene; polyhydroxyethylmethacrylate (HEMA); polydimethylsiloxane; polyacrylamide; polyimide; and block-copolymers. Preferred substrates for the device include silicon, silica, glass, and polymers. The substrate may also be a combination of any of the aforementioned substrate materials.

In order to generate a plurality of reactive sites, such as a parallel array of microchannels, the substrate material first has to be cleaned to remove contaminants such as solvent stains, dust, or organic residues. A variety of cleaning procedures can be used depending on the substrate material and origin of contaminants. These include wet immersion processes (for example, RCA1+2, "pyranha", solvents), dry vapor phase cleaning, thermal treatment, plasma or glow discharge techniques, polishing with abrasive compounds, short-wavelength light exposure, ultrasonic agitation and treatment with supercritical fluids.

Channels can then be formed on the surface of the substrate by either (1) bulk micromachining, (2) sacrificial micromachining, (3) LIGA (high aspect ratio plating) or (4) other techniques, or any combination thereof. Such techniques are well known in the semiconductor and microelectronics industries and are described in, for example, Ghandi, *VLSI Fabrication Principles*, Wiley (1983) and Sze, *VLSI Technology, 2nd. Ed.*, McGraw-Hill (1988); Wolf and Taube, *Silicon Processing for the VLSI Era, Vol. 1*, Lattice Press (1986), and Madou, *Fundamentals of Microfabrication*, CRC Press (1997).

In bulk micromachining, large portions of the substrate are removed to form rectangular or v-shaped grooves comprising the final dimensions of the microchannels. This process is usually carried out with standard photolithographic techniques involving spin-coating of resist materials, illumination through lithography masks followed by wet-chemical development and posttreatment steps such as descumming and post-baking. The resulting resist pattern is then used as an etch resist material for subsequent wet or dry etching of the bulk material to form the desired topographical structures. Typical resist materials include positive and negative organic resists (such as Kodak 747, PR102), inorganic materials (such as polysilicon, silicon nitride) and biological etch resists (for example Langmuir-Blodgett films and two-dimensional protein crystals such as the S-layer of *Sulfolobus acidocladarius*). Pattern transfer into the substrate and resist stripping occurs via wet-chemical and dry etching techniques including plasma etching, reactive ion etching, sputtering, ion-beam-assisted chemical etching and reactive ion beam etching.

In one embodiment of the invention, for instance, a photoresist may be spincoated onto a cleaned 4 inch Si(110) wafer. Ultraviolet light exposure through a photomask onto the photoresist then results in a pattern of channels in the photoresist, exposing a pattern of strips of the silicon underneath. Wet-chemical etching techniques can then be applied to etch the channel pattern into the silicon. Next, a thin layer of titanium can be coated on the surface. A thin layer of gold is then coated on the surface via thermal or electron beam evaporation. Standard resist stripping follows. (Alternatively, the gold-coating could be carried out after the strip resist.)

Figure 2:
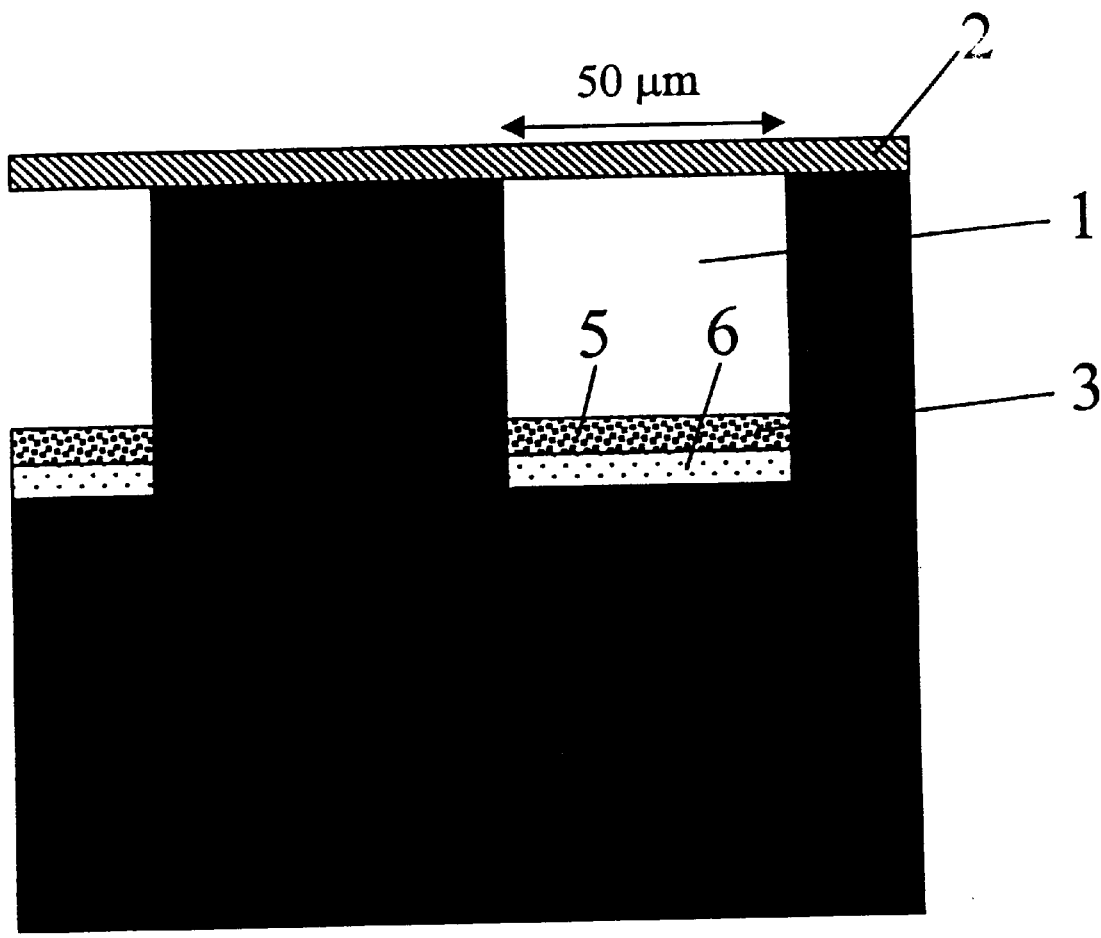
FIG. 2 shows a cross section of a covered microchannel array fabricated by bulk micromachining.

FIG. 2 shows a cross section view of one example of a microchannel array fabricated by bulk micromachining. A microchannel 1 in substrate 3 is covered by a glass cover 2. At the bottom of the microchannel, the surface of the substrate 3 is covered with a coating 5, separated by an interlayer 6.

In sacrificial micromachining, the substrate is left essentially untouched. Various thick layers of other materials are built up by vapor deposition, plasma-enhanced chemical vapor deposition (PECVD) or spin coating and selectively remain behind or are removed by subsequent processing steps. Thus, the resulting channel walls are chemically different from the bottom of the channels and the resist material remains as part of the microdevice. Typical resist materials for sacrificial micromachining are silicon nitride ($Si_3N_4$), polysilicon, thermally grown silicon oxide and organic resists such as SU-8 and polyimides allowing the formation of high aspect-ratio features with straight sidewalls.

Figure 3:
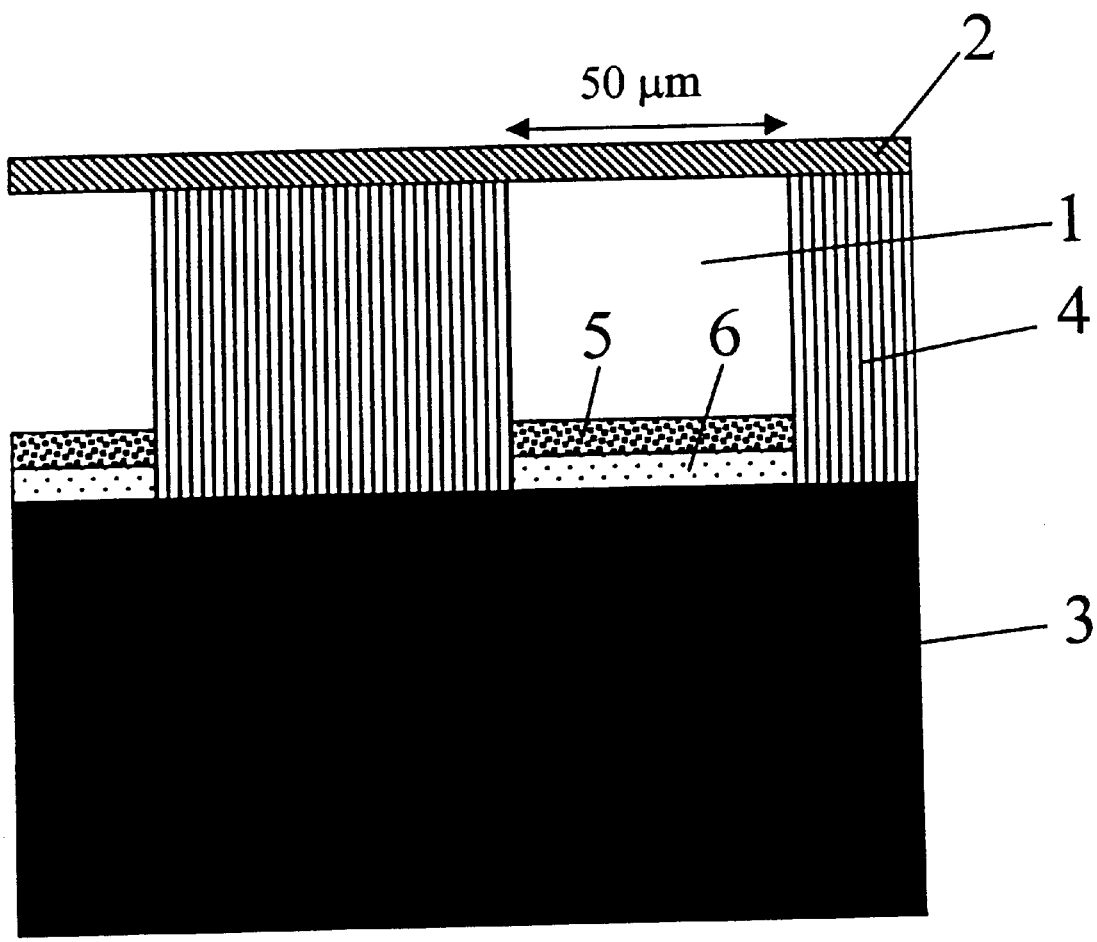
FIG. 3 shows a cross section of a covered microchannel array fabricated by sacrificial micromachining.

FIG. 3 shows a cross section view of one example of a microchannel array that has been fabricated by sacrificial micromachining. Microchannel 1 has walls that consist of photoresist 4 and a floor that comprises a substrate 3 that is covered with a coating 5 plus an interlayer 6. A glass cover 2 covers the microchannel 1.

In high-aspect ratio plating or LIGA, three-dimensional metal structures are made by high-energy X-ray radiation exposures on materials coated with X-ray resists. Subsequent electrodeposition and resist removal result in metal structures that can be used for precision plastic injection molding. These injection-molded plastic parts can be used either as the final microdevice or as lost molds. The LIGA process has been described by Becker et al., *Microelectron Engineering* (1986) 4:35–56 and Becker et al., *Naturwissenschaften* (1982) 69:520–523.

Alternative techniques for the fabrication of microchannel arrays include focused ion-beam (FIB) milling, electrostatic discharge machining (EDM), ultrasonic drilling, laser ablation (U.S. Pat. No. 5,571,410), mechanical milling and thermal molding techniques. One skilled in the art will recognize that many variations in microfabrication or micromachining techniques may be used to construct the device of the present invention.

In one embodiment, transparent or translucent covers are attached to the substrate via anodic bonding or adhesive coatings, resulting in microchannel arrays with inlet and outlet ports. In a preferred embodiment, the microchannel covers are glass, especially Pyrex or quartz glass. In alternative embodiments, a cover which is neither transparent nor translucent may be bonded or otherwise attached to the substrate to enclose the microchannels. In other embodiments the cover may be part of a detection system to monitor the interaction between biological moieties immobilized within the channel and an analyte. Alternatively, a polymeric cover may be attached to a polymeric substrate channel array by other means, such as by the application of heat with pressure or through solvent-based bonding.

One particular embodiment of a covered microchannel array is illustrated by FIG. 1. In this device, a transparent glass cover 2 covers most of the length, although not all, of each of the parallel microchannels of the array. Since in this particular embodiment the microchannels do not extend fully to the edge of the substrate, the incomplete coverage of the channel length provides an inlet and outlet port for each of the microchannels.

Attachment of a cover to the microchannel array can precede formation of the organic thinfilm on the reactive sites. If this is the case, then the solution which contains the components of the organic thinfilm (typically an organic solvent) can be applied to the interior of the channels via microfabricated dispensing systems that have integrated microcapillaries and suitable entry/exit ports. Alternatively, the organic thinfilms can be deposited in the microchannels prior to enclosure of the microchannels. For these embodiments, organic thinfilms such as monolayers can optionally be transferred to the inner microchannel surfaces via simple immersion or through microcontact printing (see PCT Publication WO 96/29629). In a most preferred embodiment, the organic thinfilm in all of the microchannels is identical. In such a case, simple immersion of the microchannel array or incubation of all of the microchannel interiors with the same fluid containing the thinfilm components is sufficient.

The volume of each enclosed microchannel may optionally be from about 5 nanoliters to about 300 nanoliters. In a preferred embodiment, the volume of an enclosed microchannel of the invention device is between 10 and 50 nanoliters.

Volumes of fluid may be moved through each microchannel by a number of standard means known to those skilled in the art. The sophisticated means required for moving fluids through microfluidic devices and mixing in microtiter plates are not needed for the microchannel array of the present invention. Simple liquid exchange techniques commonly used with capillary technologies will suffice. For instance, fluid may be moved through the channel using standard pumps. Alternatively, more sophisticated methods of fluid movement through the microchannels such as electro-osmosis may be employed (for example, see U.S. Pat. No. 4,908,112).

In one embodiment of the present invention, bulk-loading dispensing devices can be used to load all microchannels of the device at once with the same fluid. Alternatively, integrated microcapillary dispensing devices may be microfabricated out of glass or other substrates to load fluids separately to each microchannel of the device.

After formation of a microchannel, the sides, bottom, or cover of the microchannel or any portion or combination thereof, can then be further chemically modified to achieve the desired bioreactive and biocompatible properties.

The reactive sites of the device may optionally further comprise a coating between a substrate and its organic thinfilm. This coating may either be formed on the substrate or applied to the substrate. The substrate can be modified with a coating by using thin-film technology based, for example, on physical vapor deposition (PVD), thermal processing, or plasma-enhanced chemical vapor deposition (PECVD). Alternatively, plasma exposure can be used to directly activate or alter the substrate and create a coating. For instance, plasma etch procedures can be used to oxidize a polymeric surface (i.e., polystyrene or polyethylene to expose polar functionalities such as hydroxyls, carboxylic acids, aldehydes and the like).

The coating is optionally a metal film. Possible metal films include aluminum, chromium, titanium, tantalum, nickel, stainless steel, zinc, lead, iron, copper, magnesium, manganese, cadmium, tungsten, cobalt, and alloys or oxides thereof. In a preferred embodiment, the metal film is a noble metal film. Noble metals that may be used for a coating include, but are not limited to, gold, platinum, silver, and copper. In an especially preferred embodiment, the coating comprises gold or a gold alloy. Electron-beam evaporation may be used to provide a thin coating of gold on the surface of the substrate. In a preferred embodiment, the metal film is from about 50 nm to about 500 nm in thickness. In another embodiment, the metal film is from about 1 nm to about 1 μm in thickness.

In alternative embodiments, the coating comprises a composition selected from the group consisting of silicon, silicon oxide, titania, tantalum oxide, silicon nitride, silicon hydride, indium tin oxide, magnesium oxide, alumina, glass, hydroxylated surfaces, and polymers.

If the reactive site comprises a coating between the substrate and the organic thinfilm, then it is understood that the coating must be composed of a material for which a suitable functional group on the organic thinfilm is available. If no such coating is present, then it is understood that the substrate must be composed of a material for which a suitable functional group on the organic thinfilm is available.

It is contemplated that many coatings will require the addition of at least one adhesion layer or mediator between the coating and the substrate. For instance, a layer of titanium or chromium may be desirable between a silicon wafer and a gold coating. In an alternative embodiment, an epoxy glue such as Epo-tek 377®, Epo-tek 301-2®, (Epoxy Technology Inc., Billerica, Mass.) may be preferred to aid adherence of the coating to the substrate. Determinations as to what material should be used for the adhesion layer would be obvious to one skilled in the art once materials are chosen for both the substrate and coating. In other embodiments, additional adhesion mediators or interlayers may be necessary to improve the optical properties of the device, for instance, in waveguides for detection purposes.

Deposition or formation of the coating on the substrate (if such coatings are desired) must occur prior to the formation of organic thinfilms thereon.

The organic thinfilm on the reactive sites of the device forms a layer either on the substrate itself or on a coating covering the substrate. The organic thinfilm on which the biological moieties are immobilized is preferably less than about 20 nm thick. In some embodiments of the invention, the organic thinfilm of each of the sites may be less than about 10 nm thick.

A variety of different organic thinfilms are suitable for use in the present invention. Methods for the formation of organic thinfilms include in situ growth from the surface, deposition by physisorption, spin-coating, chemisorption, self-assembly, or plasma-initiated polymerization from gas phase. For instance, a hydrogel composed of a material such as dextran can serve as a suitable organic thinfilm on the sites of the device. In one preferred embodiment of the invention, the organic thinfilm is a lipid bilayer or lipid monolayer. In another preferred embodiment, the organic thinfilm of each of the sites of the device is a monolayer. A monolayer of polyarginine or polylysine adsorbed on a negatively charged substrate or coating is one option for the organic thinfilm. Another option is a disordered monolayer of tethered polymer chains. In a particularly preferred embodiment, the organic thinfilm is a self-assembled monolayer. A monolayer of polylysine is one option for the organic thinfilm. The organic thinfilm is most preferably a self-assembled monolayer which comprises molecules of the formula X—R—Y, wherein R is a spacer, X is a functional group that binds R to the surface, and Y is a functional group for binding proteins onto the monolayer. In an alternative preferred embodiment, the self-assembled monolayer is comprised of molecules of the formula $(X)_a R (Y)_b$ where a and b are, independently, integers equal to at least one and X, R, and Y are as previously defined. In an alternative preferred embodiment, the organic thinfilm comprises a combination of organic thinfilms such as a combination of a lipid bilayer immobilized on top of a self-assembled monolayer of molecules of the formula X—R—Y. As another example, a monolayer of polylysine can also optionally be combined with a self-assembled monolayer of molecules of the formula X—R—Y (see U.S. Pat. No. 5,629,213).

A variety of chemical moieties may function as monolayer molecules of the formula X—R—Y in the device of the present invention. However, three major classes of monolayer formation are preferably used to expose high densities of reactive omega-functionalities on the reactive sites of the device: (i) alkylsiloxane monolayers ("silanes") on hydroxylated and non-hydroxylated surfaces (as taught in, for example, U.S. Pat. No. 5,405,766, PCT Publication WO 96/38726, U.S. Pat. No. 5,412,087, and U.S. Pat. No. 5,688,642); (ii) alkyl-thiol/dialkyldisulfide monolayers on noble metals (preferably Au(111)) (as, for example, described in Allara et al., U.S. Pat. No. 4,690,715; Bamdad et al., U.S. Pat. No. 5,620,850; Wagner et al., *Biophysical Journal*, 1996, 70:2052–2066); and (iii) alkyl monolayer formation on oxide-free passivated silicon (as taught in, for example, Linford et al., *J. Am. Chem. Soc.,* 1995, 117:3145–3155, Wagner et al., *Journal of Structural Biology,* 1997, 119:189–201, U.S. Pat. No. 5,429,708). One of ordinary skill in the art, however, will recognize that many possible moieties may be substituted for X, R, and/or Y, dependent primarily upon the choice of substrate, coating, and affinity tag. Many examples of monolayers are described in Ulman, *An Introduction to Ultrathin Organic Films: From Langmuir-Blodgett to Self Assembly*, Academic press (1991).

In one embodiment, the monolayer comprises molecules of the formula $(X)_a R(Y)_b$ wherein a and b are, independently, equal to an integer between 1 and about 200. In a preferred embodiment, a and b are, independently, equal to an integer between 1 and about 80. In a more preferred embodiment, a and b are, independently, equal to 1 or 2. In a most preferred embodiment, a and b are both equal to 1 (molecules of the formula X—R—Y).

If the sites of the invention device comprise a self-assembled monolayer of molecules of the formula $(X)_a R (Y)_b$, then R may optionally comprise a linear or branched hydrocarbon chain from about 1 to about 400 carbons long. The hydrocarbon chain may comprise an alkyl, aryl, alkenyl, alkynyl, cycloalkyl, alkaryl, aralkyl group, or any combination thereof. If a and b are both equal to one, then R is typically an alkyl chain from about 3 to about 30 carbons long. In a preferred embodiment, if a and b are both equal to one, then R is an alkyl chain from about 8 to about 22 carbons long and is, optionally, a straight alkane. However, it is also contemplated that in an alternative embodiment, R may readily comprise a linear or branched hydrocarbon chain from about 2 to about 400 carbons long and be interrupted by at least one hetero atom. The interrupting hetero groups can include —O—, —CONH—, —CONHCO—, —NH—, —CSNH—, —CO—, —CS—, —S—, —SO—, —$(OCH_2CH_2)_n$— (where n=1–20), —$(CF_2)_n$— (where n=1–22), and the like. Alternatively, one or more of the hydrogen moieties of R can be substituted with deuterium. In alternative, less preferred, embodiments, R may be more than about 400 carbons long.

X may be chosen as any group which affords chemisorption or physisorption of the monolayer onto the surface of the substrate (or the coating, if present). For instance, if the substrate or coating is a metal or metal alloy, X, at least prior to incorporation into the monolayer, is preferably an asymmetrical or symmetrical disulfide, sulfide, diselenide, selenide, thiol, isonitrile, selenol, a trivalent phosphorus compound, isothiocyanate, isocyanate, xanthanate, thiocarbamate, a phosphine, a amine, thio acid or dithio acid. This embodiment is especially preferred when the substrate, or coating if used, is a noble metal such as gold, silver, or platinum.

If the substrate of the device is a material such as silicon, silicon oxide, indium tin oxide, magnesium oxide, alumina, quartz, glass, or silica, then the device of one embodiment of the invention comprises an X that, prior to incorporation into said monolayer, is a monohalosilane, dihalosilane, trihalosilane, trialkoxysilane, dialkoxysilane, or a monoalkoxysilane. Among these silanes, trichlorosilane and trialkoxysilane are particularly preferred.

In a preferred embodiment of the invention, the substrate is selected from the group consisting of silicon, silicon dioxide, indium fin oxide, alumina, glass, and titania; and X, prior to incorporation into said monolayer, is selected from the group consisting of a monohalosilane, dihalosilane, trihalosilane, trichlorosilane, trialkoxysilane, dialkoxysilane, monoalkoxysilane, carboxylic acid, and phosphate.

In another preferred embodiment of the invention, the substrate of the device is silicon and X is an olefin.

In still another preferred embodiment of the invention, the coating (or the substrate if no coating is present) is titania or tantalum oxide and X is a phosphate.

In other embodiments, the surface of the substrate (or coating thereon) is composed of a material such as titanium oxide, tantalum oxide, indium tin oxide, magnesium oxide, or alumina where X is a carboxylic acid or alkylphosphoric acid. Alternatively, if the surface of the substrate (or coating thereon) of the device is copper, then X may optionally be a hydroxamic acid.

If the substrate used in the invention is a polymer, then in many cases a coating on the substrate such as a copper coating will be included in the device. An appropriate functional group X for the coating would then be chosen for use in the device. In an alternative embodiment comprising a polymer substrate, the surface of the polymer may be plasma-modified to expose desirable surface functionalities for monolayer formation. For instance, EP 780423 describes the use of a monolayer molecule that has an alkene X functionality on a plasma exposed surface. Still another possibility for the invention device comprised of a polymer is that the surface of the polymer on which the monolayer is formed is functionalized due to copolymerization of appropriately functionalized precursor molecules.

Another possibility is that prior to incorporation into the monolayer, X can be a free-radical-producing moiety. This functional group is especially appropriate when the surface on which the monolayer is formed is a hydrogenated silicon surface. Possible free-radical producing moieties include, but are not limited to, diacylperoxides, peroxides, and azo compounds. Alternatively, unsaturated moieties such as unsubstituted alkenes, alkynes, cyano compounds and isonitrile compounds can be used for X, if the reaction with X is accompanied by ultraviolet, infrared, visible, or microwave radiation.

In alternative embodiments, X, prior to incorporation into the monolayer, may be a hydroxyl, carboxyl, vinyl, sulfonyl, phosphoryl, silicon hydride, or an amino group.

The component, Y, of the monolayer is responsible for binding a biological moiety onto the monolayer. In a preferred embodiment of the invention, the Y group is either highly reactive (activated) towards the biological moiety (or its affinity tag) or is easily converted into such an activated form. In a preferred embodiment, the coupling of Y with the biological moiety occurs readily under normal physiological conditions not detrimental to the biological activity of the biological moiety. The functional group Y may either form a covalent linkage or a noncovalent linkage with the biological moiety (or its affinity tag, if present). In a preferred embodiment, the functional group Y forms a covalent linkage with the biological moiety or its affinity tag. It is understood that following the attachment of the biological moiety (with or without an affinity tag) to Y, the chemical nature of Y may have changed. Upon attachment of the biological moiety, Y may even have been removed from the organic thinfilm.

In one embodiment of the present invention, Y is a functional group that is activated in situ before attachment of the biological moiety. Possibilities for this type of functional group include, but are not limited to, such simple moieties such as a hydroxyl, carboxyl, amino, aldehyde, carbonyl, methyl, methylene, alkene, alkyne, carbonate, aryliodide, or a vinyl group. Appropriate modes of activation for these simple functional groups would be known by one of ordinary skill in the art. Alternatively, Y can comprise a functional group that requires photoactivation prior to becoming activated enough to trap the biological moiety.

In an especially preferred embodiment of the device of the present invention, Y is a highly reactive functional moiety compatible with monolayer formation and needs no in situ activation prior to reaction with the biological moiety or its affinity tag. Such possibilities for Y include, but are not limited to, maleimide, N-hydroxysuccinimide (Wagner et al., *Biophysical Journal,* 1996, 70:2052–2066), nitrilotriacetic acid (U.S. Pat. No. 5,620,850), activated hydroxyl, haloacetyl, bromoacetyl, iodoacetyl, activated carboxyl, hydrazide, epoxy, aziridine, sulfonylchloride, trifluoromethyldiaziridine, pyridyldisulfide, N-acylimidazole, imidazolecarbamate, vinylsulfone, succinimidylcarbonate, arylazide, anhydride, diazoacetate, benzophenone, isothiocyanate, isocyanate, imidoester, fluorobenzene, and biotin.

Figure 4:
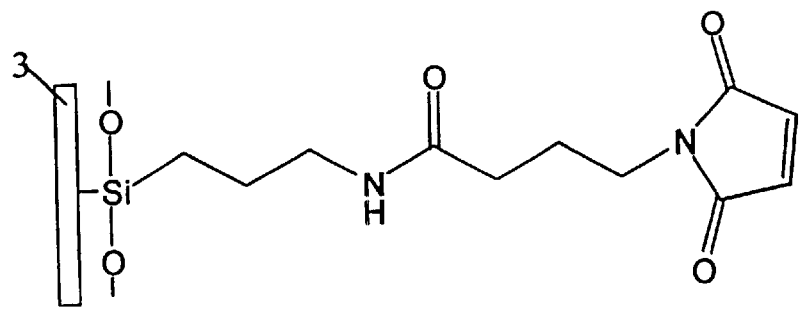
FIG. 4 shows a thiolreactive monolayer on a substrate.

FIG. 4 shows one example of a monolayer on a substrate 3. In this example, substrate 3 comprises glass. The monolayer is thioreactive because it bears a maleimidyl functional group Y.

Figure 5:
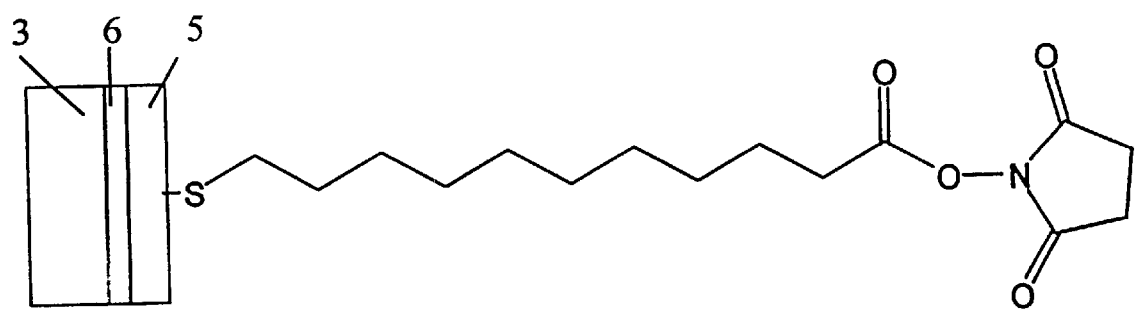
FIG. 5 shows an aminoreactive monolayer on a coated substrate.

FIG. 5 shows another example of a monolayer on a substrate 3 which is silicon. In this case, however, a thinfilm gold coating 5 covers the surface of the substrate 3. Also, in this embodiment, a titanium adhesion interlayer 6 is used to adhere the coating 5 to the substrate 3. This monolayer is aminoreactive because it bears an N-hydroxysuccinimidyl functional group Y.

In an alternative embodiment, Y is selected from the group of simple functional moieties. Possible Y functional groups include, but are not limited to, —OH, —NH$_2$, —COOH, —COOR, —RSR, —PO$_4^{-3}$, —OSO$_3^{-2}$, —SO$_3-$, —COO—, —SOO—, —CONR$_2$, —CN, —NR$_2$, and the like.

The monolayer molecules of the present invention can optionally be assembled on the surface in parts. In other words, the monolayer need not necessarily be constructed by chemisorption or physisorption of molecules of the formula X—R—Y to the surface of the substrate (or coating). Instead, in one embodiment, X may be chemisorbed or physisorbed to the surface of the substrate (or coating) alone first. Then, R or even just individual components of R can be attached to X through a suitable chemical reaction. Upon completion of addition of the spacer R to the X moiety already immobilized on the surface, Y can be attached to the ends of the monolayer molecule through a suitable covalent linkage.

Not all monolayer molecules at a given reactive site need to be identical. Some may consist of mixed monolayers. For instance, the monolayer of an individual reactive site may optionally comprise at least two different X—R—Y molecules. This second X—R—Y molecule may immobilize the same or a different biological moiety. In addition, many of the monolayer molecules, X—R—Y, of a reactive site may have failed to attach any biological moiety.

As another alternative of the invention, the monolayer of an individual reactive site can comprise a second organic molecule that is of the formula, X—R—V where R is the spacer, X is the functional group that binds R to the surface, and V is a moiety resistant to the non-specific binding of biomolecules. One of ordinary skill in the art will recognize that the possibilities for V will vary depending upon the nature of the biological moiety chosen for the sites of the device. For instance, functional groups V which are resistant to non-specific protein binding are used if the immobilized biological moiety of the device comprises protein. The nature of V will be somewhat dependent upon the type of proteins and solutions used. For instance, V may comprise a hydroxyl, saccharide, or oligo/polyethylene glycol moiety (EP Publication 780423).

As a still further alternative of the invention device, the device may further comprise at least one unreactive site devoid of any biological moiety that comprises a monolayer of molecules of the formula X—R—V, where R is the spacer, X is the functional group that binds R to the surface, and V is the moiety resistant to the non-specific binding of biomolecules. In this embodiment, the unreactive site does not comprise any monolayers of molecules of the formula X—R—Y.

Regardless of the nature of the monolayer molecules, in some cases it can be desirable to provide crosslinking between molecules of the monolayer. In general, this confers additional stability to the monolayer. Methods of crosslinking such monolayers are known to those skilled in the art (see Ullman, *An Introduction to Ultrathin Organic Films: From Langmuir-Blodgett to Self-Assembly,* Academic Press (1991).

In addition to facilitating binding of the biological moiety to the substrate, functionalization of the substrate with organic thinfilms is desirable for other reasons as well. Many biological moieties and protein, in particular, are susceptible to disruption of their bioactivities at surface interfaces. Proteins are prone to both denaturation and undesirable, non-specific binding at the solid/liquid interface. Other biological moieties such as small molecule ligands may have less problematic interactions with the substrate surface interface, but upon approach of the biological binding partner, presumably a protein, to the small molecule in an assay, problems of inactivation become highly relevant. A highly-ordered organic monolayer can effectively "carpet" the surface of the substrate or coating, protecting the biological moiety from contact with the surface. These highly-ordered, self-assembled monolayers are preferred in the present invention. Additionally, the spacer R creates distance between the immobilized biological moiety and the surface.

Following formation of organic thinfilm on the reactive sites of the invention device, the biological moieties are immobilized on the monolayers. A solution containing the biological moiety to be immobilized can be exposed to the bioreactive, organic thinfilm covered sites of the microdevice by either dispensing the solution by means of microfabricated adapter systems with integrated microcapillaries and entry/exit ports. Such a dispensing mechanism would be suitable, for instance, if the reactive sites of the device were in covered, parallel microchannels. Alternatively, the biological moieties may be transferred to uncovered sites of the device by using one of the arrayers based on capillary dispensing systems which are well known in the art and even commercially available. These dispensing systems are preferably automated and computer-aided. A description of and building instructions for an example of a microarrayer comprising an automated capillary system can be found on the internet at http ://cmgm.stanford.edu/pbrown/array.html and http://cmgm.stanford.edu/pbrown/mguide/index.html. The use of other printing techniques is also anticipated. Following attachment of the biological moieties to the monolayer, unreacted Y-functional groups are preferably quenched prior to use of the device.

In an alternative embodiment of the invention, the reactive sites of the device are not contained within microchannels. For instance, the reactive sites of the invention device may instead form an array of reactive sites like some of those described in the co-pending U.S. patent applications "Arrays of Protein-Capture Agents and Methods of Use Thereof", filed on Jul. 14, 1999, with the identifier 24406–0006, for the inventors Peter Wagner, Steffen Nock, Dana Ault-Riche, and Christian Itin, and "Arrays of Proteins and Methods of Use Thereof", filed on Jul. 14, 1999, with the identifier 24406–0004 P1, for the inventors Peter Wagner, Dana Ault-Riche, Steffen Nock, and Christian Itin, both of which are herein incorporated by reference in their entirety.

(c) Affinity Tags and Immobilization of the Biological Moieties

In a preferred embodiment, the reactive sites of the device further comprise an affinity tag that enhances immobilization of the biological moiety onto the organic thinfilm. The use of an affinity tag to immobilize the biological moiety typically provides several advantages. An affinity tag can confer enhanced binding or reaction of the biological moiety with the functionalities on the organic thinfilm, such as Y if the organic thinfilm is a an X—R—Y monolayer as previously described. This enhancement effect may be either kinetic or thermodynamic. The affinity tag/thinfilm combination used on the reactive sites of the device preferably allows for immobilization of the biological moieties in a manner which does not require harsh reaction conditions that are adverse to the stability or function of the biological moiety. In most embodiments, immobilization to the organic thinfilm in aqueous, biological buffers is ideal.

An affinity tag also preferably offers immobilization on the organic thinfilm that is specific to a designated site or location on the biological moiety (site-specific immobilization). For this to occur, attachment of the affinity tag to the biological moiety must be site-specific. Site-specific immobilization helps ensure that the active site or binding site of the immobilized biological moiety, such as the antigen-binding site of an antibody, remains accessible to ligands in solution. Another advantage of immobilization through affinity tags is that it allows for a common immobilization strategy to be used with multiple, different biological moieties.

The affinity tag is optionally attached directly, either covalently or noncovalently, to the biological moiety. In an alternative embodiment, however, the affinity tag is either covalently or noncovalently attached to an adaptor which is either covalently or noncovalently attached to the biological moiety.

In a preferred embodiment, the affinity tag comprises at least one amino acid. The affinity tag may be a polypeptide comprising at least two amino acids which is reactive with the functionalities of the organic thinfilm. Alternatively, the affinity tag may be a single amino acid which is reactive with the organic thinfilm. Examples of possible amino acids which could be reactive with an organic thinfilm include cysteine, lysine, histidine, arginine, tyrosine, aspartic acid, glutamic acid, tryptophan, serine, threonine, and glutamine. If the biological moiety of a reactive site to be immobilized is a protein, then the polypeptide or amino acid affinity tag is preferably expressed as a fusion protein with the biological moiety. Amino acid affinity tags provide either a single amino acid or a series of amino acids that can interact with the functionality of the organic thinfilm, such as the Y-functional group of the self-assembled monolayer molecules. Amino acid affinity tags can be readily introduced into recombinant proteins to facilitate oriented immobilization by covalent binding to the Y-functional group of a monolayer or to a functional group on an alternative organic thinfilm.

The affinity tag may optionally comprise a poly(amino acid) tag. A poly(amino acid) tag is a polypeptide that comprises from about 2 to about 100 residues of a single amino acid, optionally interrupted by residues of other amino acids. For instance, the affinity tag may comprise a poly-cysteine, polylysine, poly-arginine, or poly-histidine. Amino acid tags are preferably composed of two to twenty residues of a single amino acid, such as, for example, histidines, lysines, arginines, cysteines, glutamines, tyrosines, or any combination of these. According to a preferred embodiment, an amino acid tag of one to twenty amino acids includes at least one to ten cysteines for thioether linkage; or one to ten lysines for amide linkage; or one to ten arginines for coupling to vicinal dicarbonyl groups. One of ordinary skill in the art can readily pair suitable affinity tags with a given functionality on an organic thinfilm.

The position of the amino acid tag can be at the amino-terminus or the carboxy-terminus of the biological moiety of a reactive site which is a protein, or anywhere in-between, as long as the active site or binding site of the biological moiety remains in a position accessible for ligand interaction. Where compatible with the protein chosen, affinity tags introduced for protein purification are preferentially located at the C-terminus of the recombinant protein to ensure that only full-length proteins are isolated during protein purification. For instance, if intact antibodies are used on the reactive sites, then the attachment point of the affinity tag on the antibody is preferably located at a C-terminus of the effector (Fc) region of the antibody. If scFvs are used on the reactive sites, then the attachment point of the affinity tag is also preferably located at the C-terminus of the molecules.

Affinity tags may also contain one or more unnatural amino acids. Unnatural amino acids can be introduced using suppressor tRNAs that recognize stop codons (i.e., amber) (Noren et al., *Science*, 1989, 244:182–188; Ellman et al., *Methods Enzym.*, 1991, 202:301–336; Cload et al., *Chem. Biol.*, 1996, 3:1033–1038). The tRNAs are chemically amino-acylated to contain chemically altered ("unnatural") amino acids for use with specific coupling chemistries (i.e., ketone modifications, photoreactive groups).

In an alternative embodiment the affinity tag can comprise an intact protein, such as, but not limited to, glutathione S-transferase, an antibody, avidin, or streptavidin.

Other protein conjugation and immobilization techniques known in the art may be adapted for the purpose of attaching affinity tags to the biological moiety. For instance, in an alternative embodiment of the device, the affinity tag may be an organic bioconjugate which is chemically coupled to the biological moiety of interest. Biotin or antigens may be chemically cross linked to the biological moiety. Alternatively, a chemical crosslinker may be used that attaches a simple functional moiety such as a thiol or an amine to the surface of a biological moiety to be immobilized on a reactive site of the device. Alternatively, protein synthesis or protein ligation techniques known to those skilled in the art may be used to attach an affinity tag to a biological moiety which is a protein. For instance, intein-mediated protein ligation may optionally be used to attach the affinity tag to the biological moiety (Mathys, et al., *Gene* 231:1–13, 1999; Evans, et al., *Protein Science* 7:2256–2264, 1998).

In an alternative embodiment of the invention, the organic thinfilm of each of the reactive sites comprises, at least in part, a lipid monolayer or bilayer, and the affinity tag comprises a membrane anchor. Optionally, the lipid monolayer or bilayer is immobilized on a self-assembled monolayer.

Figure 6:
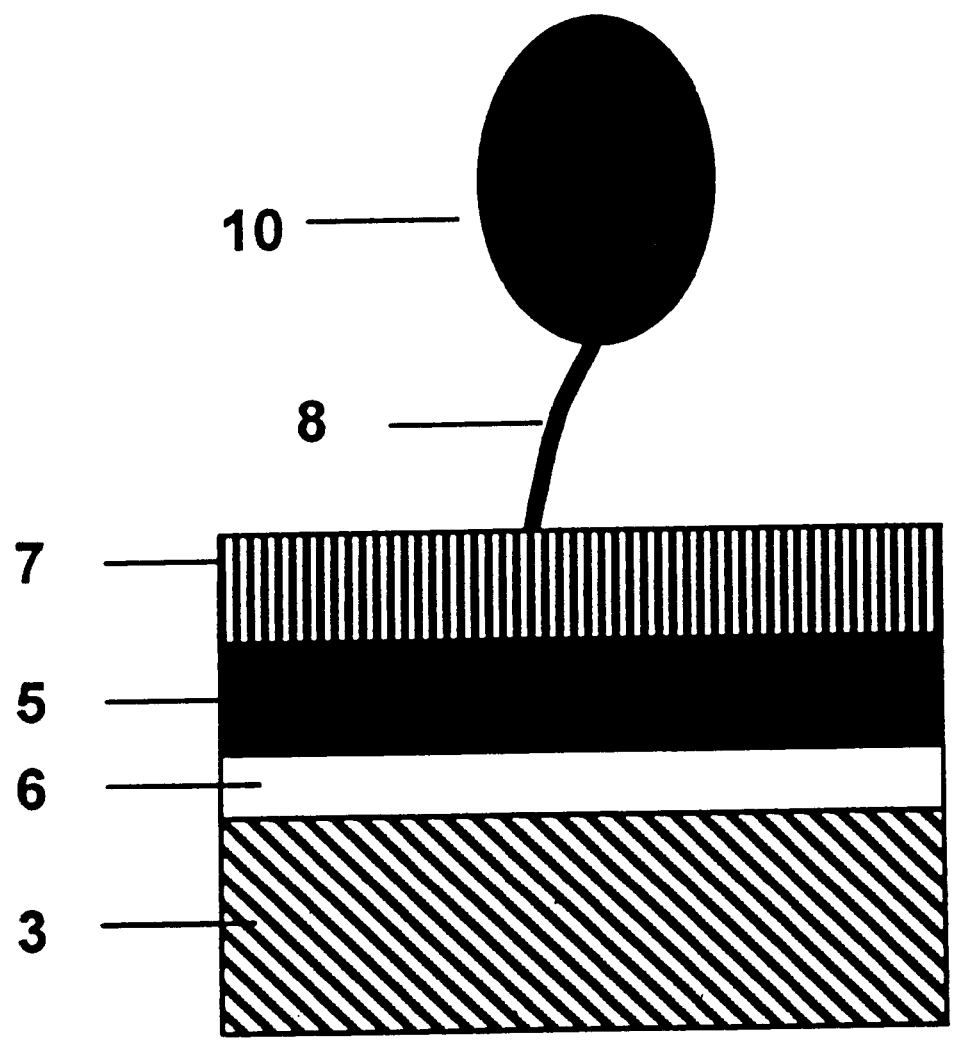
FIG. 6 shows a biological moiety immobilized on a monolayer-coated substrate via an affinity tag.

FIG. 6 shows a biological moiety 10 immobilized on a monolayer 7 on a substrate 3. An affinity tag 8 connects the biological moiety 10 to the monolayer 7. The monolayer 7 is formed on a coating 5 separated from the surface of the substrate 3 by an interlayer 6.

Figure 7:
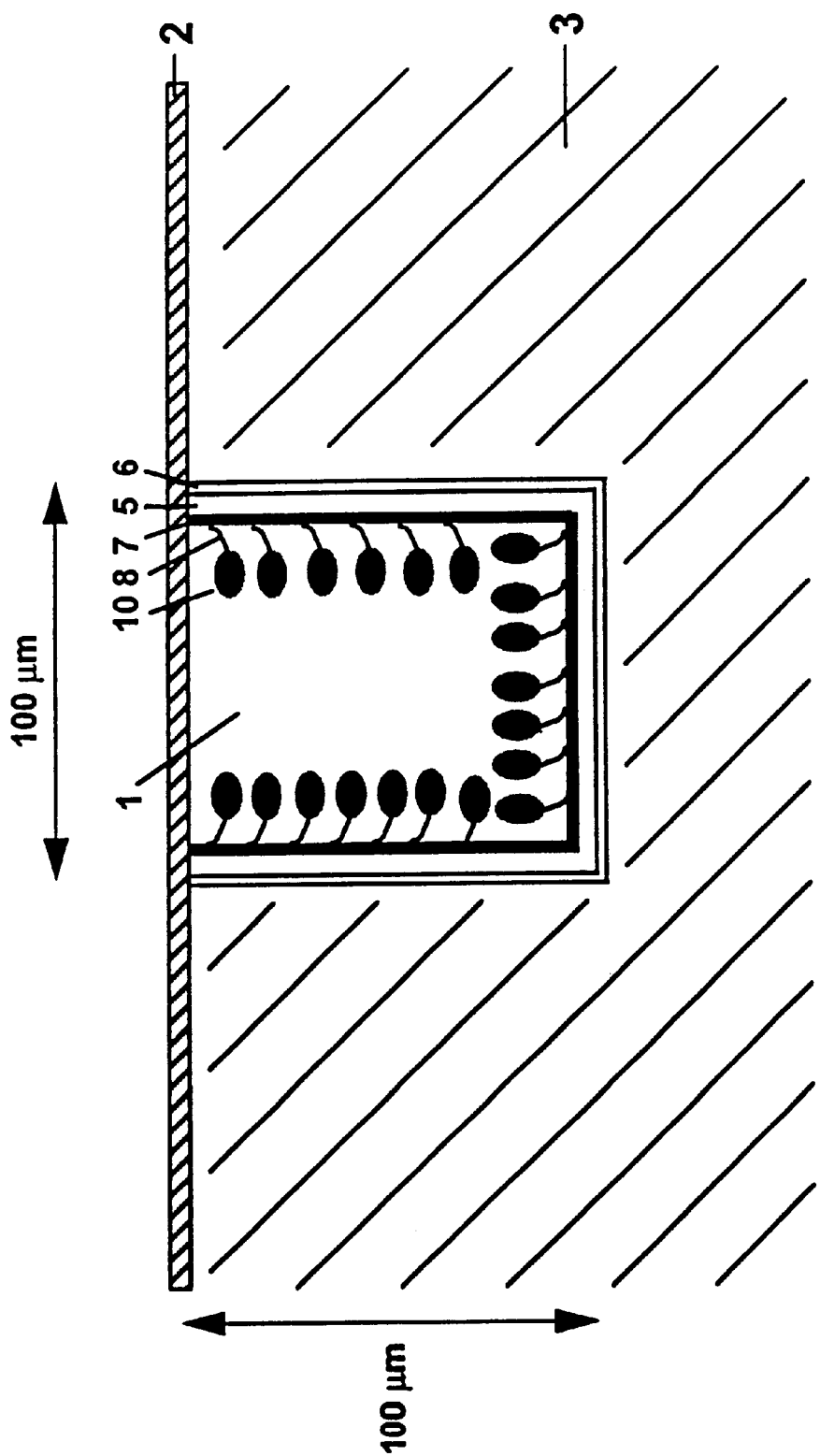
FIG. 7 shows a cross section view of a biomolecule-coated microchannel in a microchannel array device.

FIG. 7 shows a cross section of a biomolecule-coated microchannel of one embodiment of a microchannel array device. The microchannel 1 is covered by a glass cover 2. The walls of the microchannel are comprised of substrate 3, coated first with an interlayer 6, then with a coating 5, then with an organic monolayer 7 and finally, with the biological moiety 10 via the affinity tag 8.

In an alternative embodiment of the invention, no affinity tag is used to immobilize the biological moieties onto the organic thinfilm. An amino acid, nucleotide, or other moiety (such as a carbohydrate moiety) inherent to the biological moiety itself may instead be used to tether the protein to the reactive group of the organic thinfilm. In preferred embodiments, the immobilization is site-specific with respect to the location of the site of immobilization on the biological moiety. For instance, the sulfhydryl group on the C-terminal region of the heavy chain portion of a Fab' fragment generated by pepsin digestion of an antibody, followed by selective reduction of the disulfide between monovalent Fab' fragments, may be used as the affinity tag. Alternatively, a carbohydrate moiety on the Fc portion of an intact antibody can be oxidized under mild conditions to an aldehyde group suitable for immobilizing the antibody on a monolayer via reaction with a hydrazide-activated Y group on the monolayer. Examples of immobilization of proteins without any affinity tag can be found in Wagner et al., *Biophys. J.*, 70:2052–2066, 1996.

(d) Adaptors

Another embodiment of the devices of the present invention comprises an adaptor that links the affinity tag to the immobilized biological moiety. The additional spacing of the protein from the surface of the substrate (or coating) that is afforded by the use of an adaptor is particularly advantageous since some biological moieties such as proteins are known to be prone to surface inactivation. The adaptor may optionally afford some additional advantages as well. For instance, the adaptor may help facilitate the attachment of the biological moiety to the affinity tag. In another embodiment, the adaptor may help facilitate the use of a particular detection technique with the device. One of ordinary skill in the art will be able to choose an adaptor which is appropriate for a given affinity tag. For instance, if the affinity tag is streptavidin, then the adaptor could be a biotin molecule that is chemically conjugated to the protein which is to be immobilized.

In a preferred embodiment, the adaptor is a protein. In a preferred embodiment, the affinity tag, adaptor, and biological moiety together compose a fusion protein. Such a fusion protein may be readily expressed using standard recombinant DNA technology. Adaptors which are proteins are especially useful to increase the solubility of the protein of interest and to increase the distance between the surface of the substrate or coating and the protein of interest. Use of an adaptor which is a protein can also be very useful in facilitating the preparative steps of protein purification by affinity binding prior to immobilization on the device. Examples of possible adaptors which are proteins include glutathione-S-transferase (GST), maltose-binding protein, chitin-binding protein, thioredoxin, green-fluorescent protein (GFP). GFP can also be used for quantification of surface binding. If the biological moiety immobilized on the reactive sites of the device is an antibody or antibody fragment comprising an Fc region, then the adaptor may optionally be protein G, protein A, or recombinant protein A/G (a gene fusion product secreted from a non-pathogenic form of Bacillus which contains four Fc binding domains from protein A and two from protein G).

Figure 8:
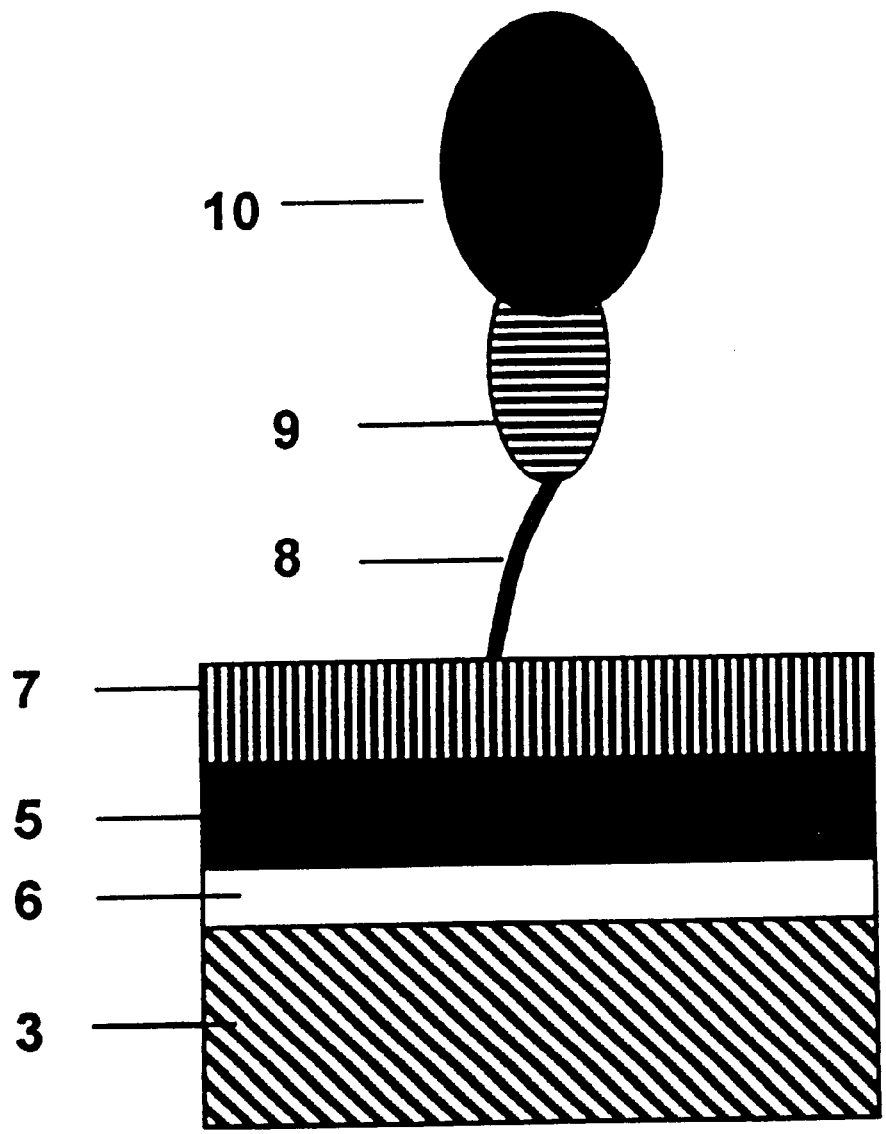
FIG. 8 shows a biological moiety immobilized on a monolayer-coated substrate via an affinity tag and an adaptor molecule.

FIG. 8 shows a biological moiety 10 immobilized on a monolayer 7 via both an affinity tag 8 and an adaptor molecule 9. The monolayer 7 has been formed on a coating 5 on a substrate 3. An interlayer 6 is also used between the coating 5 and the substrate 3.

(e) The Immobilized Biological Moieties and Preparation Thereof

In one embodiment of the present invention, the biological moiety of one reactive site differs from the biological moiety of a second reactive site on the same device. In a preferred embodiment, the device comprises at least about 10 different immobilized biological moieties. In an especially preferred embodiment, the device comprises at least about 100 different immobilized biological moieties.

In a preferred embodiment, the biological moieties immobilized on the sites of the invention device are proteins. Although proteins are the preferred biological moieties of the present invention, the immobilized biological moiety may optionally instead comprise a polynucleotide, a peptide nucleic acid, a hormone, an antigen, an epitope, or any small organic molecule which either has or is suspected of having a physiological function.

In another embodiment of the present invention, although the biological moiety of one reactive site is different from that of another, the two biological moieties are related. In a preferred embodiment the biological moieties are members of the same protein family. The different biological moieties may be functionally related or just suspected of being functionally related. In another embodiment, however, the function of the biological moieties may not be entirely known. In these cases, the different biological moieties may either share a similarity in structure or sequence or be suspected of sharing a similarity in structure or sequence. In one embodiment, the different immobilized biological moieties may simply be fragments of different members of the same protein family. In another embodiment, the biological moieties may be known isozymes.

Examples of protein families include, but are not limited to, a receptor families (examples: growth factor receptors, catecholamine receptors, amino acid derivative receptors, cytokine receptors, lectins), ligand families (examples: cytokines, serpins), enzyme families (examples: proteases, kinases, phosphatases, ras-like GTPases, hydrolases), and transcription factors (examples: steroid hormone receptors, heat-shock transcription factors, zinc-finger proteins, leucine-zipper proteins, homeodomain proteins). In one embodiment, the different immobilized proteins are all HIV proteases or hepatitis C virus (HCV) proteases. In other embodiments of the invention, the immobilized proteins on the reactive sites of the invention device are all hormone receptors, neurotransmitter receptors, extracellular matrix receptors, antibodies, DNA-binding proteins, intracellular signal transduction modulators and effectors, apoptosis-related factors, DNA synthesis factors, DNA repair factors, DNA recombination factors, or cell-surface antigens.

In an alternative preferred embodiment, the biological moieties of the sites of the invention device are protein-capture agents. In another preferred embodiment, the biological moieties of the reactive sites or microchannels of the device are all antibodies or antibody fragments.

In an alternative embodiment of the invention device, the biological moieties of the different reactive sites on the device are identical to one another.

The biological moieties immobilized on the device may be produced by any of the variety of means known to those of ordinary skill in the art.

In preparation for immobilization to the sites of the devices of the present invention, a biological moiety which is a protein can optionally be expressed from recombinant DNA either in vivo or in vitro. The cDNA of the protein to be immobilized on the device is cloned into an expression vector (many examples of which are commercially available) and introduced into cells of the appropriate organism for expression. A broad range of host cells and expression systems may be used to produce the proteins to be immobilized on the device. For in vivo expression of the proteins, cDNAs can be cloned into commercial expression vectors (Qiagen, Novagen, Clontech, for example) and introduced into an appropriate organism for expression. Expression in vivo may be done in bacteria (for example, *Escherichia coli*), plants (for example, *Nicotiana tabacum*), lower eukaryotes (for example, *Saccharomyces cerevisiae, Saccharomyces pombe, Pichia pastoris*), or higher eukaryotes (for example, bacculovirus-infected insect cells, insect cells, mammalian cells). For in vitro expression PCR-amplified DNA sequences are directly used in coupled in vitro transcription/translation systems (for instance: *Escherichia coli* S30 lysates from T7 RNA polymerase expressing, preferably protease-deficient strains; wheat germ lysates; reticulocyte lysates (Promega, Pharmacia, Panvera)). The choice of organism for optimal expression depends on the extent of post-translational modifications (i.e., glycosylation, lipid-modifications) desired. One of ordinary skill in the art will be able to readily choose which host cell type is most suitable for the protein to be immobilized and application desired.

DNA sequences encoding amino acid affinity tags and adaptor protein sequences are engineered into the expression vectors such that the genes of interest can be cloned in frame either 5' or 3' of the DNA sequence encoding the affinity tag and adaptor.

The expressed proteins are purified by affinity chromatography using commercially available resins.

Preferably, production of families of related proteins involves parallel processing from cloning to protein expression and protein purification. cDNAs for the protein of interest will be amplified by PCR using cDNA libraries or EST (expressed sequence tag) clones as templates. Any of the in vitro or in vivo expression systems described above can then be used for expression of the proteins to be immobilized on the device.

*Escherichia coli*-based protein expression is generally the method of choice for soluble proteins that do not require extensive post-translational modifications for activity. Extracellular or intracellular domains of membrane proteins will be fused to protein adaptors for expression and purification.

The entire approach can be performed using 96-well assay plates. PCR reactions are carried out under standard conditions. Oligonucleotide primers contain unique restriction sites for facile cloning into the expression vectors. Alternatively, the TA cloning system (Clontech) can be used. Expression vectors contain the sequences for affinity tags and the protein adaptors. PCR products are ligated into the expression vectors (under inducible promoters) and introduced into the appropriate competent *Escherichia coli* strain by calcium-dependent transformation (strains include: XL-1 blue, BL21, SG13009(lon-)). Transformed *Escherichia coli* cells are plated and individual colonies transferred into 96-array blocks. Cultures are grown to mid-log phase, induced for expression, and cells collected by centrifugation. Cells are resuspended containing lysozyme and the membranes broken by rapid freeze/thaw cycles, or by sonication. Cell debris is removed by centrifugation and the supernatants transferred to 96-tube arrays. The appropriate affinity matrix is added, protein of interest bound and nonspecifically bound proteins removed by repeated washing steps using 12–96 pin suction devices and centrifugation. Alternatively, magnetic affinity beads and filtration devices can be used (Qiagen). The proteins are eluted and transferred to a new 96-well array. Protein concentrations are determined and an aliquot of each protein is spotted onto a nitrocellulose filter and verified by Western analysis using an antibody directed against the affinity tag. The purity of each sample is assessed by SDS-PAGE and silver staining or mass spectrometry. Proteins are snap-frozen and stored at −80° C.

Saccharomyces cerevisiae allows for core glycosylation and lipid modifications of proteins. The approach described above for Escherichia coli can be used with slight modifications for transformation and cell lysis. Transformation of Saccharomyces cerevisiae is by lithium-acetate and cell lysis is either by lyticase digestion of the cell walls followed by freeze-thaw, sonication or glass-bead extraction. Variations of post-translational modifications can be obtained by different yeast strains (i.e. Saccharomyces pombe, Pichia pastoris).

The advantage of the bacculovirus system or mammalian cells are the wealth of post-translational modifications that can be obtained. The bacculo-system requires cloning of viruses, obtaining high titer stocks and infection of liquid insect cell suspensions (cells are SF9, SF21). Mammalian cell-based expression requires transfection and cloning of cell lines. Soluble proteins are collected from the medium while intracellular or membrane bound proteins require cell lysis (either detergent solubilization, freeze-thaw). Proteins can then be purified analogous to the procedure described for Escherichia coli.

For in vitro translation the system of choice is Escherichia coli lysates obtained from protease-deficient and T7 RNA polymerase overexpressing strains. Escherichia coli lysates provide efficient protein expression (30–50 μg /ml lysate). The entire process is carried out in 96-well arrays. Genes of interest are amplified by PCR using oligonucleotides that contain the gene-specific sequences containing a T7 RNA polymerase promoter and binding site and a sequence encoding the affinity tag. Alternatively, an adaptor protein can be fused to the gene of interest by PCR. Amplified DNAs can be directly transcribed and translated in the Escherichia coli lysates without prior cloning for fast analysis. The proteins are then isolated by binding to an affinity matrix and processed as described above.

Alternative systems which may be used include wheat germ extracts and reticulocyte extracts. In vitro synthesis of membrane proteins and or post-translationally modified proteins will require reticulocyte lysates in combination with microsomes.

In one preferred embodiment of the invention, the proteins immobilized on the sites of the device are antibodies. Optionally, the immobilized proteins may be monoclonal antibodies. The production of monoclonal antibodies against specific protein targets is routine using standard hybridoma technology. In fact, numerous monoclonal antibodies are available commercially.

As an alternative to obtaining antibodies or antibody fragments which have been produced by cell fusion or from continuous cell lines, the antibody moieties may be expressed in bacteriophage. Such antibody phage display technologies are well known to those skilled in the art. The bacteriophage expression systems allow for the random recombination of heavy- and light-chain sequences, thereby creating a library of antibody sequences which can be selected against the desired antigen. The expression system can be based on bacteriophage λ or, more preferably, on filamentous phage. The bacteriophage expression system can be used to express Fab fragments, Fv's with an engineered intermolecular disulfide bond to stabilize the $V_H$-$V_L$ pair (dsFv's), scFvs, or diabody fragments.

The antibody genes of the phage display libraries may be from pre-immunized donors. For instance, the phage display library could be a display library prepared from the spleens of mice previously immunized with a mixture of proteins (such as a lysate of human T-cells). Immunization can optionally be used to bias the library to contain a greater number of recombinant antibodies reactive towards a specific set of proteins (such as proteins found in human T-cells). Alternatively, the library antibodies may be derived from naive or synthetic libraries. The naive libraries have been constructed from spleens of mice which have not been contacted by external antigen. In a synthetic library, portions of the antibody sequence, typically those regions corresponding to the complementarity determining regions (CDR) loops, have been mutagenized or randomized.

The phage display method involves batch-cloning the antibody gene library into a phage genome as a fusion to the gene encoding one of the phage coat proteins (pIII, pVI, or pVIII). The pIII phage protein gene is preferred. When the fusion product is expressed it is incorporated into the mature phage coat. As a result, the antibody is displayed as a fusion on the surface of,the phage and is available for binding and hence, selection, on a target protein. Once a phage particle is selected as bearing an antibody-coat protein fusion with the desired affinity towards the target protein, the genetic material within the phage particle which corresponds to the displayed antibody can be amplified and sequenced or otherwise analyzed.

In a preferred embodiment, a phagemid is used as the expression vector in the phage display procedures. A phagemid is a small plasmid vector that carries gene III with appropriate cloning sites and a phage packaging signal and contains both host and phage origins of replication. The phagemid is unable to produce a complete phage as the gene III fusion is the only phage gene encoded on the phagemid. A viable phage can be produced by infecting cells containing the phagemid with a helper phage containing a defective replication origin. A hybrid phage emerges which contains all of the helper phage proteins as well as the gene III-rAb fusion. The emergent phage contains the phagemid DNA only.

In a preferred embodiment of the invention, the recombinant antibodies used in phage display methods of preparing antibody fragments for the devices of the invention are expressed as genetic fusions to the bacteriophage gene III protein on a phagemid vector. For instance, the antibody variable regions encoding a single-chain Fv fragment can be fused to the amino terminus of the gene III protein on a phagemid. Alternatively, the antibody fragment sequence could be fused to the amino terminus of a truncated pIII sequence lacking the first two N-terminal domains. The phagemid DNA encoding the antibody-pIII fusion is preferably packaged into phage particles using a helper phage such as M13KO7 or VCS-M13, which supplies all structural phage proteins.

To display Fab fragments on phage, either the light or heavy (Fd) chain is fused via its C-terminus to pIII. The partner chain is expressed without any fusion to pIII so that both chains can associate to form an intact Fab fragment.

Any method of selection may be used which separates those phage particles which do bind the target protein from those which do not. The selection method must also allow for the recovery of the selected phages. Most typically, the phage particles are selected on an immobilized target protein. Some phage selection strategies known to those skilled in the art include the following: panning on an immobilized antigen; panning on an immobilized antigen using specific elution; using biotinylated antigen and then selecting on a streptavidin resin or streptavidin-coated magnetic beads; affinity purification; selection on Western blots (especially useful for unknown antigens or antigens difficult to purify); in vivo selection; and pathfinder selection. If the selected phage particles are amplified between selection rounds, multiple iterative rounds of selection may optionally be performed.

Elution techniques will vary depending upon the selection process chosen, but typical elution techniques include washing with one of the following solutions: HCl or glycine buffers; basic solutions such as triethylamine; chaotropic agents; solutions of increased ionic strength; or DTT when biotin is linked to the antigen by a disulfide bridge. Other typical methods of elution include enzymatically cleaving a protease site engineered between the antibody and gene III, or by competing for binding with excess antigen or excess antibodies to the antigen.

In the preparation of the devices of the invention, phage display methods analogous to those used for antibody fragments may be used for other proteins which are to be immobilized on a device of the invention as long as the protein is of suitable size to be incorporated into the phagemid or alternative vector and expressed as a fusion with a bacteriophage coat protein. Phage display techniques using non-antibody libraries typically make use of some type of protein host scaffold structure which supports the variable regions. For instance, β-sheet proteins, α-helical handle proteins, and other highly constrained protein structures have been used as host scaffolds.

Alternative display vectors may also be used to produce proteins which are immobilized on the sites of the device. Polysomes, stable protein-ribosome-mRNA complexes, can be used to replace live bacteriophage as the display vehicle for recombinant antibody fragments or other proteins (Hanes and Pluckthun, *Proc. Natl. Acad. Sci USA*, 94:4937–4942, 1997). The polysomes are formed by preventing release of newly synthesized and correctly folded protein from the ribosome. Selection of the polysome library is based on binding of the antibody fragments or other proteins which are displayed on the polysomes to the target protein. mRNA which encodes the displayed protein or antibody having the desired affinity for the target is then isolated. Larger libraries may be used with polysome display than with phage display.

(e) Uses of the Devices

Methods for using the devices of the present invention are provided by other aspects of the invention. The devices of the present invention are particularly well-suited for use in drug development, such as in high-throughput drug screening. Other uses include medical diagnostics and biosensors. The devices of the invention are also useful for functional proteomics. In each case, a plurality of biological moieties or drug candidates or analytes can be screened for potential biological interactions in parallel.

In one aspect of the invention, a method for screening a plurality of different biological moieties in parallel for their ability to interact with a component of a fluid sample is provided. This method comprises delivering the fluid sample to the reactive sites of one of the invention devices where each of the different biological moieties is immobilized on a different site of the device, and then detecting for the interaction of the component with the immobilized biological moiety at each reactive site. In a preferred embodiment, each of the reactive sites is in a microchannel oriented parallel to microchannels of other reactive sites on the device, wherein the microchannels are microfabricated into or onto the substrate.

The invention device is suitable for assaying a catalytic reaction of an enzyme, a binding event, or even a translocation by a membrane protein through a lipid bilayer. Possible interactions towards which the present invention may be directed include, but are not limited to, antibody/antigen, antibody/hapten, enzyme/substrate, carrier protein/substrate, lectin/carbohydrate, receptor/hormone, receptor/effector, protein/DNA, protein/RNA, complementary strands of nucleic acid, repressor/inducer, or the like. The assayed interaction may be between a potential drug candidate and a plurality of potential drug targets. For instance, a synthesized organic compound may be tested for its ability to act as an inhibitor to a family of immobilized receptors. The devices are also highly suitable for assaying for protein-protein interactions in general.

One embodiment of the present invention provides for a method of screening a plurality of biological moieties in parallel for their ability to react with a component of a fluid sample, comprising delivering the fluid sample to the reactive sites of a device of the present invention, wherein each of the different biological moieties is immobilized on a different reactive site of the device and detecting, either directly or indirectly, for formation of product of the reaction of the component with the immobilized biological moiety at each reactive site.

Another embodiment of the invention provides a method for screening a plurality of biological moieties in parallel for their ability to bind a component of a fluid sample. This method comprises the following steps: delivering the fluid sample to the reactive sites of the invention device, wherein each of the different biological moieties is immobilized on a different site of the device; optionally, washing the reactive site remove unbound or nonspecifically bound components of the sample from the reactive sites; and detecting, either directly or indirectly, for the presence or amount of the component retained at each reactive site.

An alternative method for screening a plurality of biological moieties for their ability to bind a component of a fluid sample comprises first adding a known ligand of the biological moieties to the fluid sample and then delivering the fluid sample to the reactive sites of the invention device, where each of the different biological moieties is immobilized on a different site of the device. As an optional next step, the reactive sites may be washed with fluid that does not contain either the known ligand or the component in order to elute unbound or nonspecifically bound molecules of the known ligand and the component (or other components from the sample) from the reactive sites of the device. A final step of the method comprises detecting the presence or amount of the known ligand retained at each reactive site, and comparing retention of the known ligand at each reactive site with retention of the known ligand at the same or an identical reactive site in the absence of the component.

A wide range of detection methods is applicable to the methods of the invention. As desired, detection may be either quantitative or qualitative. The invention device can be interfaced with optical detection methods such as absorption in the visible or infrared range, chemoluminescence, and fluorescence (including lifetime, polarization, fluorescence correlation spectroscopy (FCS), and fluorescence-resonance energy transfer (FRET)). Furthermore, other modes of detection such as those based on optical waveguides (PCT Publication WO 96/26432 and U.S. Pat. No. 5,677,196), surface plasmon resonance, surface charge sensors, and surface force sensors are compatible with many embodiments of the invention. Alternatively, technologies such as those based on Brewster angle microscopy (Schaaf et al., Langmuir, 3:1131–1135 (1987)) and ellipsometry (U.S. Pat. Nos. 5,141,311 and 5,116,121; Kim, Macromolecules, 22:2682–2685 (1984)) can be used in conjunction with the devices of the invention. Quartz crystal microbalances and desorption processes (see for example, U.S. Pat. No. 5,719,060) provide still other alternative detection means suitable for at least some embodiments of the invention device. An example of an optical biosensor system compatible both with some devices of the present invention and a variety of non-label detection principles including surface plasmon resonance, total internal reflection fluorescence (TIRF), Brewster Angle microscopy, optical waveguide lightmode spectroscopy (OWLS), surface charge measurements, and ellipsometry can be found in U.S. Pat. No. 5,313,264.

Figure 9:
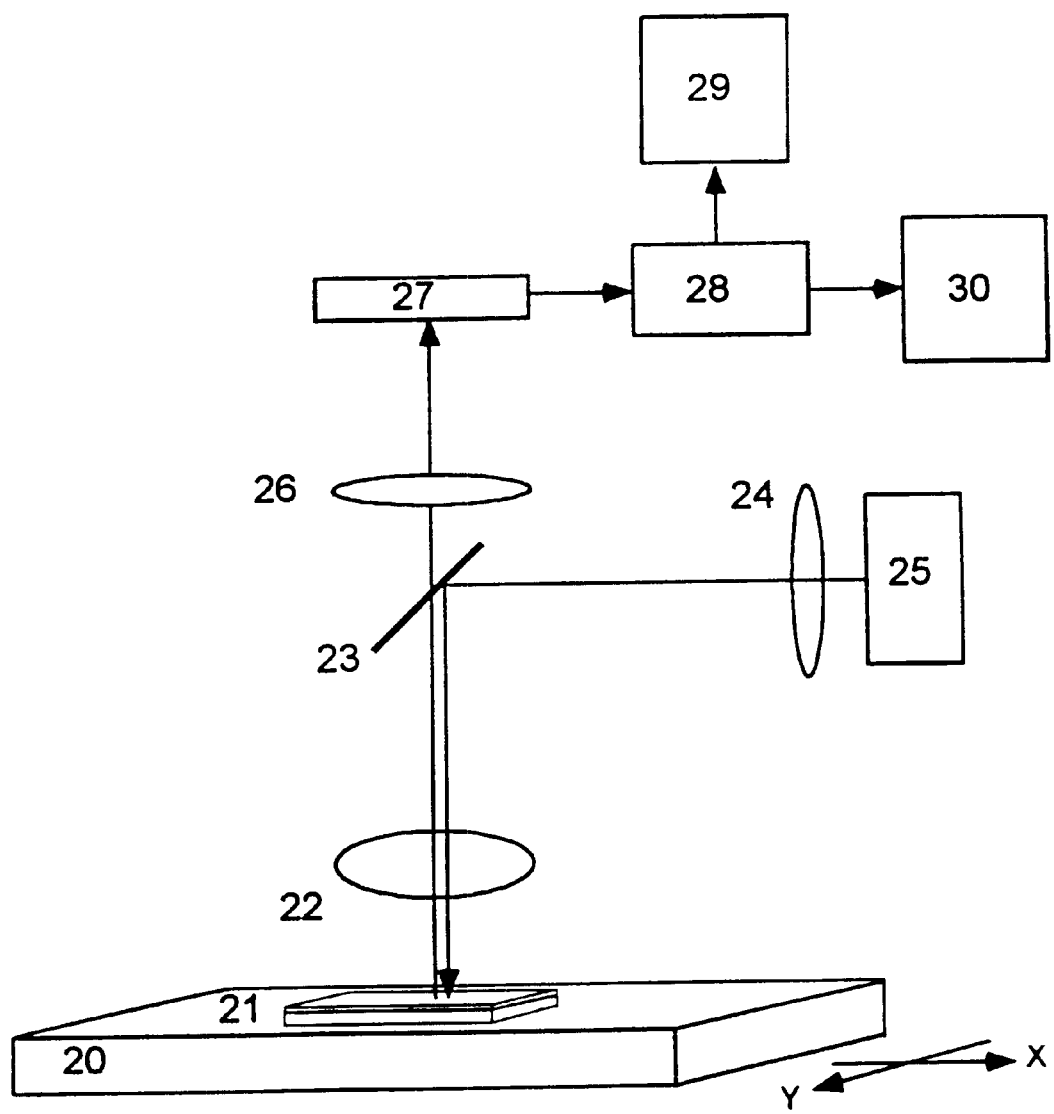
FIG. 9 shows a schematic diagram of a fluorescence detection unit which may be used to monitor interaction of the immobilized biological moieties of a microchannel array with an analyte.

FIG. 9 shows a schematic diagram of one type of fluorescence detection unit which may be used to monitor the interaction of immobilized biological moieties of a microchannel array with an analyte. In the illustrated detection unit, the microchannel array device 21 is positioned on a base plate 20. Light from a 100 W mercury arc lamp 25 is directed through an excitation filter 24 and onto a beam splitter 23. The light is then directed through a lens 22, such as a Micro Nikkor 55 mm 1:2:8 lens, and onto the microchannels of the device 21. Fluorescence emission from the device returns through the lens 22 and the beam splitter 23. After also passing through an emission filter 26, the emission is received by a cooled CCD camera 27, such as the Slowscan TE/CCD-1024SF&SB (Princeton Instruments). The camera is operably connected to a CPU 28, which is, in turn, operably connected to a VCR 29 and monitor 30.

To test the specificity of a drug candidate, its interaction with multiple members of a protein family is determined. Members of the protein family are separately immobilized in microchannels. The drug candidate's ability to interfere with protein activity, such as binding, catalytic conversion, or translocation of a ligand through a lipid bilayer, is then determined.

In another example, to test a drug candidate's ability to interfere with a protein binding event, the drug candidate and a known ligand of a member of the protein family that is labeled by a chemically-conjugated fluorescent moiety are delivered in a fluid sample into each microchannel of the device. After a short incubation period, the microchannels are flushed with fluid which lacks both the drug candidate and the ligand. The amount of fluorescent ligand remaining in each of the microchannels (and presumably bound to the protein molecules of that microchannel) can then be detected by using a fluorescence detector/quantifier with optical access to the reactive site, either through a transparent or translucent cover or substrate.

To test a drug candidate's ability to interfere with a catalytic conversion of a ligand, drug candidate and ligand are delivered into the microchannel in a fluid sample and changes in the chromogenic or fluorescent properties can be detected by using an optical detector/quantifier with optical access to the reactive site, either through a transparent or translucent cover or substrate.

In a more general sense, the present invention provides for a method of screening the ability of a drug candidate to inhibit the reaction of a plurality of members of a protein family with their substrate, comprising the following steps: combining the drug candidate and the substrate in a fluid sample; delivering the fluid sample to the reactive sites of a device of the present invention, wherein each different member of the protein family in immobilized to a different reactive site; and detecting, either directly or indirectly, for the inhibition of product formation at each reactive site.

To test a drug candidate's ability to interfere with the translocation of a ligand through a lipid bilayer, drug candidate and ligand are delivered in a fluid sample to each microchannel. After a short incubation period the microchannels may be flushed with fluid lacking ligand and any inhibition of passage of the ligand through the lipid bilayer is determined by measuring changes in fluorescence, absorption, or electrical charge.

In an alternative embodiment of the invention, the device of the invention is used to screen a plurality of components, each in separate fluid samples, for their ability to interact with a biological moiety. The method of this embodiment comprises first delivering each of the different fluid samples to separate reactive sites of the invention device, wherein the separate reactive sites of the device each comprise the immobilized biological moiety. The next step comprises detecting, either directly or indirectly, for the interaction of the immobilized biological moiety at each reactive site with the component delivered to that reactive site. Preferably, each of the reactive sites is in a microchannel oriented parallel to microchannels of other reactive sites on the device, wherein the microchannels are microfabricated into or onto the substrate. As before, the interaction being assayed by this method may be any type of interaction normally observed for biological moieties including a catalytic reaction of an enzyme, a binding event, or a translocation by a membrane protein through a lipid bilayer.

One embodiment of the invention provides a method for screening a plurality of different proteins in parallel for their ability to interact with a particular protein, comprising the following steps: delivering different fluid samples, each containing at least one of the different proteins, to separate reactive sites of the device of the invention, wherein the particular protein is immobilized on each of the separate reactive sites; and detecting, either directly or indirectly, for the interaction of the particular protein with the different proteins at each of the reactive sites.

An alternative embodiment of the invention provides for a method for screening a plurality of drug candidates in parallel for their ability to inhibit a reaction of an enzyme with its substrate. This method first involves adding the enzyme's substrate to a plurality of fluid samples, each of which contains at least one of the drug candidates of interest. Next, each of the fluid samples is delivered to a reactive site of the invention device, preferably a microchannel array. In this embodiment, each reactive site of the device features the immobilized enzyme. Finally, inhibition of product formation at each reactive site (due to the presence of the drug candidate in the solution) is monitored.

Another aspect of the invention provides a method for screening a plurality of binding candidates in parallel for their ability to bind a biological moiety. This method comprises first delivering different fluid samples, each containing at least one of the binding candidates, to the reactive sites of the invention device, wherein the separate reactive sites each comprise the immobilized biological moiety. An optional next step comprises washing the reactive sites with fluid which does not contain the binding candidate in order to elute unbound or nonspecifically bound binding candidates, and detecting, either directly or indirectly, for the presence or amount of said binding candidate retained at each reactive site.

An alternative method for screening a plurality of binding candidates in parallel for their ability to bind a biological moiety is also provided by the present invention comprises the following: adding a known ligand of the biological moiety to a plurality of fluid samples, each of the fluid samples containing at least one of the binding candidates; delivering a different fluid sample to each of the reactive sites of the invention device, wherein the separate reactive sites of the device each comprise the immobilized biological moiety; optionally, washing said reactive sites with fluid that contains neither the known ligand nor a binding candidate in order to elute unbound molecules from each from the reactive sites; detecting the presence of the known ligand retained at each reactive site; and comparing the retention of the known ligand in the presence of the binding candidate with retention of the known ligand in the absence of the binding candidate.

The present invention also provides for a method of pairing a plurality of different proteins with their substrates. In this method, a fluid sample comprising a substrate of a known enzyme family is first delivered to the reactive sites of the invention device where each reactive site of the device comprises a different protein immobilized on the site. Next, any suitable detection means may be used to detect, either directly or indirectly, for the presence of product formed by the reaction of the substrate with the protein of each reactive site. This method is useful for identifying the function of multitudes of proteins with no known function.

In another aspect of the invention, a method for pairing a plurality of different proteins with their ligands is provided. This method comprises delivering a fluid sample comprising a ligand of a known protein family to the reactive sites of the invention device, wherein each reactive site of the device comprises a different immobilized protein; optionally, washing the reactive sites with fluid that does not contain the ligand to remove unbound ligand from the reactive sites of the device; and detecting, either directly or indirectly, the presence or amount of the ligand retained at each reactive site. This method is useful for identifying to which protein family a protein of unknown function may belong.

Still another embodiment of the invention provides a method for detecting in a fluid sample the presence of a plurality of analytes. The steps of this method comprise delivering the fluid sample to the reactive sites of the invention device, wherein a biological moiety which reacts with at least one of the analytes is immobilized on each of the reactive sites, and detecting for the interaction of the analyte with the immobilized biological moiety at each reactive site.

Another method for detecting in a fluid sample the presence of a plurality of analytes, comprises the following steps: delivering the fluid sample to the reactive sites of the invention device, wherein a biological moiety which binds at least one of the analytes is immobilized on each of the reactive sites; optionally, washing said reactive sites with an analyte-free fluid to remove unbound or nonspecifically bound analyte from each reactive site; and detecting, either directly or indirectly, the presence or amount of analyte retained at each reactive site.

The methods for the parallel detection of a plurality of analytes are applicable to a variety of diagnostic uses. The analytes may optionally be compounds in a body fluid or cellular extract whose presence or amount is indicative of a disease condition in an organism. In one example, the origin of the analytes may be a pathogen which has infected the organism. Alternatively, the analytes may be expression products of a cell or population of cells in the organism. Such a method can be useful in the evaluation of a tumor or other disease state in a tissue of the organism.

EXAMPLES

The following specific examples are intended to illustrate the invention and should not be construed as limiting the scope of the claims:

Example 1

Fabrication of a Microchannel Array by Bulk Micromachining

In a preferred embodiment microchannel arrays are fabricated via standard microstereolithography into the device material (bulk micromachining). Alternative techniques include surface-micromachining and LIGA (injection molding). Usually, a computer-aided design pattern (reflecting the final channel geometries) is transferred to a photomask using standard techniques, which is then used to transfer the pattern onto a silicon wafer coated with photoresist.

In a typical example, the device ("chip"), with lateral dimensions of 50×15 mm, contains a series of 100 parallel channels separated with a spacing of 250 $\mu$m. Each channel is 5 mm long and has a cross-section of 100×100 $\mu$m. The channel volume is 50 nl. 4" diameter Si(100) wafers (Virginia Semiconductor). Si(100) wafers are first cleaned in a 3:1 mixture of $H_2SO_4$, conc.: 30% $H_2O_2$ (90° C., 10 min), rinsed with deionized water (18 M$\Omega$cm), finally passivated in 1% aqueous HF, and singed at 150° C. for 30 min. After the wafer has been spincoated with polymethyl methacrylate PMMA as positive photoresist and prebaked for 25 minutes at 90° C., it is exposed using a Karl Suss contact printer and developed according to standard protocols. The wafer is then dried and postbaked at 110° C. for 25 min. Deep silicon reactive ion etching (RIE) is used to anisotropically dry-etch the channel features into the bulk material resulting in high aspect ratio, vertical sidewall features in the silicon (etch rate 2.5 $\mu$m/min). In the next step, the wafer is primed with a 20 nm thick titanium layer, followed by a 200 nm thick gold layer both layers deposited using electron-beam evaporation (5 Å/s). After resist stripping (acetone) and a short plasma treatment, the device is covered and sealed with a 50 $\mu$m thin glass cover (pyrex 7740) using low-temperature field assisted glass-silicon bonding resulting in a multichannel array with inlet and outlet ports. The gold-coated channel walls can then be further chemically modified to achieve the desired bioreactive and biocompatible properties (see Example 3, below).

Additional details of these procedures can be found in the following references: Madou, *Fundamentals of Microfabrication*, CRC Press (1997); Wolf and Tauber, *Silicon Processing for the VLSI Era, Vol. 1: Process Technology*, Lattice Press, (1986); and Thomson et al., *Introduction to Microlithography*, American Chemical Society, (1994).

Example 2

Fabrication of a Microchannel Array by Sacrificial Micromachining

In sacrificial micromachining, the bulk material is left, essentially untouched. Various thick layers of other materials are built up by either physical vapor deposition (PVD), plasma-enhanced chemical vapor deposition (PECVD) or spin coating and selectively remain behind or are removed by subsequent processing steps. Thus, the resulting channel walls are chemically different from the bottom of the channels and the resist material remains as part of the microdevice. Typical resist materials for sacrificial micromachining are silicon nitride ($Si_3N_4$), polysilicon, thermally grown silicon oxide and organic resists such as epoxy-based SU-8 and polyimides allowing the formation of high aspect-ratio features with straight sidewalls.

In a typical example, the device ("chip"), with lateral dimensions of 50×15 mm, contains a series of 100 parallel channels separated with a spacing of 250 µm. Each channel is 5 mm long and has a cross-section of 100×100 µm. The channel volume is 50 nl. 4" diameter Si(100) wafers (Virginia Semiconductor). Si(100) wafers are first cleaned in a 3:1 mixture of $H_2SO_4$, conc.: 30% $H_2O_2$ (90° C., 10 min), rinsed with deionized water (18 MΩcm), finally passivated in 1% aqueous HF, and singed at 150° C. for 30 min. Spincoating of the wafer with EPON SU-8 results in a 100 µm thick film that is exposed similar to Example 1, above, and developed in a propyleneglycol-monomethyletheracetate (PGMEA) solution resulting in a multi-channel structure with high-aspect ratio vertical sidewalls. Deposition of metal films (20 nm Ti, 200 nm Au) is carried out as described in Example 1, above. The device is covered with a 50 µm thin adhesive glass cover. The gold-coated channel walls can then be further chemically modified to achieve the desired bioreactive and biocompatible properties (see Example 3, below).

Additional details on sacrificial micromachining processes can be found in Lorenz, et al., *Proceedings of MME'96* (*Micro Mechanics Europe*), Barcelona, Spain, October 1996, p. 32–35.

Example 3

Synthesis of an Aminoreactive Monolayer Molecule (Following the Procedure Outlined in Wagner et al., *Biophys. J.*, 1996, 70:2052–2066)

General. $^1H$- and $^{13}C$-NMR spectra are recorded on Bruker instruments (100 to 400 MHz). Chemical shifts (δ) are reported in ppm relative to internal standard (($CH_3)_4Si$, δ=0.00 ($^1H$- and $^{13}C$-NMR)). FAB-mass spectra are recorded on a VG-SABSEQ instrument ($Cs^+$, 20 keV). Transmission infrared spectra are obtained as dispersions in KBr on an FTIR Perkin-Elmer 1600 Series instrument. Thin-layer chromatography (TLC) is performed on pre-coated silica gel 60 F254 plates (MERCK, Darmstadt, FRG), and detection was done using $Cl_2$/toluidine, $PdCl_2$ and UV-detection under $NH_3$-vapor. Medium pressure liquid chromatography (MPLC) is performed on a Labomatic MD-80 (LABOMATIC INSTR. AG, Allschwil, Switzerland) using a Buechi column (460×36 mm; BUECHI, Flawil, Switzerland), filled with silica gel 60 (particle size 15–40 µm) from Merck.

Synthesis of 11,11'-dithiobis(succinimidylundecanoate) (DSU). Sodium thiosulfate (55.3 g, 350 mmol) is added to a suspension of 11-bromo-undecanoic acid (92.8 g, 350 mmol) in 50% aqueous 1,4-dioxane (1000 ml). The mixture is heated at reflux (90° C.) for 2 h until the reaction to the intermediate Bunte salt was complete (clear solution). The oxidation to the corresponding disulfide is carried out in situ by adding iodine in portions until the solution retained with a yellow to brown color. The surplus of iodine is retitrated with 15% sodium pyrosulfite in water. After removal of 1,4-dioxane by rotary evaporation the creamy suspension is filtered to yield product 11,11'-dithiobis(undecanoic acid). Recrystallization from ethyl acetate/THF provides a white solid (73.4 g, 96.5%): mp 94° C.; $^1H$ NMR (400 MHz, $CDCl_3/CD_3OD$ 95:5): δ2.69 (t, 2H, J=7.3 Hz), 2.29 (t, 2H, J=7.5 Hz), 1.76–1.57 (m, 4H), and 1.40–1.29 (m, 12H); FAB-MS ($Cs^+$, 20 keV): m/z (relative intensity) 434 (100, $M^+$). Anal. Calcd. for $C_{22}H_{42}O_4S_2$: C, 60.79; H, 9.74; S, 14.75. Found: C, 60.95; H, 9.82; S, 14.74. To a solution of 11,11'-dithiobis(undecanoic acid) (1.0 g, 2.3 mmol) in THF (50 ml) is added N-hydroxysuccinimide (0.575 g, 5 mmol) followed by DCC (1.03 g, 5 mmol) at 0° C. After the reaction mixture is allowed to warm to 23° C. and is stirred for 36 h at room temperature, the dicyclohexylurea (DCU) is filtered. Removal of the solvent under reduced pressure and recrystallization from acetone/hexane provides 11,11'-dithiobis(succinimidylundecanoate) as a white solid. Final purification is achieved by medium pressure liquid chromatography (9 bar) using silica gel and a 2:1 mixture of ethyl acetate and hexane. The organic phase is concentrated and dried in vacuum to afford 11,11'-dithiobis (succinimidylundecanoate) (1.12 g, 78%): mp 95° C.; $^1H$ NMR (400 MHz, $CDCl_3$): δ2.83 (s, 4H), 2.68 (t, 2H, J=7.3 Hz), 2.60 (t, 2H, J=7.5 Hz), 1.78–1.63 (m, 4H), and 1.43–1.29 (m, 12H); FAB-MS ($Cs^+$, 20 keV): m/z (relative intensity) 514 (100), 628 (86, $M^+$). Anal. Calcd. for $C_{30}H_{48}N_2O_8S_2$: C, 57.30; H, 7.69; N, 4.45; S, 10.20. Found: C, 57.32; H, 7.60; N, 4.39; S, 10.25.

Example 4

Formation of an Aminoreactive Monolayer on Gold (Following the Procedure of Wagner et al., *Biophys. J.*, 1996, 70:2052–2066)

Mono layers based on 11,11'-dithiobis (succinimimidylundecanoate) (DSU) are deposited on Au(111) surfaces of microdevices described under Examples 1 and 2 by immersing them into a 1 mM solution of DSU in chloroform at room temperature for 1 hour. After rinsing with 10 volumes of solvent, the N-hydroxysuccinimide-terminated monolayer are dried under a stream of nitrogen and immediately used for protein immobilization.

Example 5

Expression and Purification of HIV Protease Variants

The HIV protease (Genebank HIVHXB2CG) is an essential component of the HIV life cycle, and a major target in anti-viral therapy. HIV protease is required for the proteolytic processing of the gag and gag-pol gene products into functional proteins. Inhibition of HIV protease prevents the production of infectious viral progeny, and hence further rounds of infection. HIV protease belongs to the family of aspartic proteases and is a symmetric homodimer with an active site formed at the interface of the two 99 amino acids long subunits. The core residues in the active site consist of a conserved tripeptide motif (Asp-Thr-Gly) (Roberts et al., *Science*, 1990, 248:358). Resistant variants of HIV protease have emerged against all inhibitors currently used. Most prevalent mutations causing resistance individually or in combination are: L10R, D30N, M46I, L63P, A71V, V82F (Kaplan et al., *Proc. Natl. Acad Sci.,* 1994, 91:5597; Ho et al., *J. Virol.* 1994, 68: 2016; Condra et al., *Nature,* 1995, 374:569; Schock et al., *J. Biol. Chem.,* 1996, 271:31957; Korant and Rizzo, *Adv. Exp. Med Biol.,* 1997, 421:279). Additional mutations that preserve protease activity are systematically generated (Loeb et al., *Nature,* 1989, 340:397).

Mutant proteases are generated by PCR mutagenesis (Weiner et al., *Gene,* 1994, 151:119) and expressed in *Escherichia coli* using two approaches: (i) mutant and wild-type protease cDNAs are cloned into a *Escherichia coli* expression vector containing a N-terminal histidine tag ($H_6$ SEQ ID NO:1; Hochuli et al., *Biotechnology* 1988, 6:1321) followed by a factor Xa cleavage site, while the stop codon of HIV protease is replaced by a sequence encoding a lysine tag ($K_6$) SEQ ID NO:2 followed by a stop codon. The resulting fusion protein is purified from inclusion bodies as described in Wondrak and Louis, *Biochemistry,* 1996, 35:12957, and the histidine tag removed by factor Xa as described in Wu et al., *Biochemistry,* 1998, 37:4518; or (ii) mutant and wild-type protease cDNAs are cloned into an *Escherichia coli* expression vector creating a fusion between HIV protease, a triglycine linker, glutathione S-transferase (GST) and a lysine-tag (HIV-GST-$K_6$). The autoprocessing site F*P at the carboxy terminus of the HIV protease is changed to F*I to prevent self-cleavage of the fusion proteins (Louis et al., *Eur. J. Biochem.,* 1991, 199:361). The resulting proteins HIV-GST-$K_6$ are purified from *Escherichia coli* lysates by standard chromatography on glutathione agarose beads and stored in an amine-free buffer at $-80°$ C. (25 mM HEPES, pH 7.5, 150 mM NaCl).

Example 6

Immobilization of Fusion Proteins on an Aminoreactive Monolayer

HIV protease variants, in the form of HIV-GST-$K_6$, and GST-$K_6$ are immobilized to the aminoreactive monolayer surface of the microchannel device (see Example 4, above). HIV-GST-$K_6$ and GST-$K_6$ are diluted to concentrations of 1 μg/ml in 25 mM HEPES buffer (pH 7.5) containing 150 mM NaCl. First, 50 μl of protein-free buffer is transferred through the channels to hydrate the monolayer surface. After 5 min of incubation, 10 μl of the corresponding protein solutions are flushed through the channels to guarantee total replacement with protein-containing solution. Immobilization is finished after 30 min at room temperature. The channels are rinsed with 50 μl immobilization buffer and subjected to analysis. Each microchannel displays a different HIV-GST-$K_6$ variant or control (GST-$K_6$). Ultrapure water with a resistance of 18 MΩcm is generally used for all aqueous buffers (purified by passage through a Barnstead Nanopure® system).

Example 7

Assay of Protease Activity in Microchannels

HIV protease requires at least a heptapeptide substrate (Moore et al., *Biochem. Biophys. Res. Commun.,* 1989, 159:420). To analyze the activity of the different HIV variants, a continuous assay based on intra-molecular fluorescence resonance energy transfer (FRET) is used. A peptide substrate corresponding to the p17–p24 cleavage site of the viral gag protein (Skalka, *Cell,* 1989, 56:911) is modified by the addition of an energy-transfer pair (Geoghegan et al., *FEBS Lett.,* 1990, 262:119): In Dns-Ser-Gln-Asn-Tyr-Pro-Ile-Val-Trp (Dns-SSQNYPIVW SEQ ID NO:3), the Dns (dansyl) and Trp groups are the N- and C-terminal extensions, respectively (Geoghegan et al.). Excitation of Trp is at 290 mm, and emission of Dns is at 575 nm. Cleavage of the peptide at the Tyr-Pro bond reduces the Dns emission and increases Trp emission at 360 nm. The modified heptapeptide; Dns-SQNYPIVW is prepared as described (Geoghegan et al.) and analyzed by amino acid analysis, nuclear magnetic resonance and mass spectrometry. The purity is checked by HPLC analysis using a Vydac C-4 column and an acetonitrile gradient in 0.1% TFA. In order to test the activity of all the HIV variants described above, each microchannel with an immobilized HIV variant (see Example 6) is filled with 20 μM of Dns-SQNYPIVW in 50 mM sodium acetate, pH 5.5, 13% glycerol, 10 mM DTT. Addition of the substrate to the immobilized proteins leads to time-dependent intensity changes in the fluorescence emission spectrum. The 360 nm Trp emission peak progressively will increase to about 2.5 times its initial intensity, while the Dns group's emission band (575 nm) will decline in intensity. This intensity change will be observed in all the channels containing active forms of the HIV variants. To control for changes in background fluorescence, GST-$K_6$ fusion protein is measured in parallel.

Competition assays can be carried out to test the specificity of the proteolysis by the HIV variants. In one assay, both Dns-SQNYPIVW and a small organic molecule that is to be tested for its potential as a drug, is delivered in a 50 mM sodium acetate, pH 5.5, 13% glycerol, 10 mM DTT solution to each channel. An organic molecule which acts as an inhibitor for a wide range of HIV protease variants will diminish the Trp emission peak increase and the Dns emission band decrease associated with reaction of the protease with the peptide substrate in a number of the microchannels. A less desirable drug candidate, on the other hand, will inhibit the reaction of the HIV protease with the peptide substrate only in selected microchannels (or none at all).

Protease inhibitors Sequinavir (Roche), Ritonavir (Abbot) or Indinavir (Merck) can also be added to the reaction buffer and used as positive controls for the specificity of inhibition. Sequinavir will inhibit all the HIV variants except those containing either the G48V or the L90M mutation. Ritonavir in contrast is unable to block the activity of the M46I, L63P, A71V, V82F and the I84V variants. Indinavir has a similar inhibition pattern like Ritonavir except that the A71V variant is not affected. In addition Indinavir is not able to decrease the activity of the L10R HIV protease variant.

These experiments demonstrate how an HIV-variant microchannel device may be used to test the inhibitory effect of small organic molecules on the activity of the HIV protease.

All documents cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A multi-channel sample detection device, comprising (a) a substrate having an upper surface;

(b) a plurality of open channels formed in or on said substrate adjacent said upper surface, each channel extending between first and second ends and having a bottom wall surface defining a substantially planar immobilization region intermediate the first and second ends;

(c) a transparent cover attached to said substrate and forming with each channel a closed channel having open first and second ends, where the first ends of the channels are linearly aligned so that said channels can each be both independently loaded with a fluid having a fluid surface and containing one or more analytes or simultaneously loaded with said fluid by simultaneously placing said aligned first open ends of said channels in contact with said fluid surface;

(d) a thinfilm having a hydrophilic display surface, and covering each immobilization region, said thinfilm being effective to resist non-specific protein binding; and, (e) a plurality of immobilization groups for immobilizing selected proteins or peptides or small molecules, said immobilization groups being attached to said thinfilm in each channel;

wherein when said liquid containing said one or more analytes is introduced into said channels to interact with said peptides or proteins or small molecules, such interactions, if any, can be observed through said transparent cover.

2. The device of claim 1, wherein at least one of said open ends is formed in said cover.

3. The device of claim 1, wherein said channel have a cross-section that is between about 10 $\mu$m and 500 $\mu$m, and a length between about 1 to 20 mm.

4. The device of claim 1, wherein said transparent cover further comprises one or more opaque regions.

* * * * *

UNITED STATES PATENT AND TRADEMARK OFFICE
CERTIFICATE OF CORRECTION

PATENT NO. : 6,596,545 B1
DATED : July 22, 2003
INVENTOR(S) : Wagner et al.

It is certified that error appears in the above-identified patent and that said Letters Patent is hereby corrected as shown below:

Column 38,
Line 58, after "channel," please replace "have" with -- has --.

Signed and Sealed this

Fourteenth Day of October, 2003

JAMES E. ROGAN
*Director of the United States Patent and Trademark Office*